(12) United States Patent
Nakamura et al.

(10) Patent No.: US 7,727,714 B2
(45) Date of Patent: Jun. 1, 2010

(54) HYPOXIA-INDUCIBLE PROTEIN 2 (HIG2), A DIAGNOSTIC MARKER FOR CLEAR CELL RENAL CELL CARCINOMA

(75) Inventors: Yusuke Nakamura, Yokohama (JP); Toyomasa Katagiri, Shinagawa-ku (JP)

(73) Assignee: Oncotherapy Science, Inc., Kanagawa (JP)

( * ) Notice: Subject to any disclaimer, the term of this patent is extended or adjusted under 35 U.S.C. 154(b) by 876 days.

(21) Appl. No.: 10/569,129

(22) PCT Filed: Aug. 20, 2004

(86) PCT No.: PCT/JP2004/012411
§ 371 (c)(1),
(2), (4) Date: Nov. 7, 2006

(87) PCT Pub. No.: WO2005/019475
PCT Pub. Date: Mar. 3, 2005

(65) Prior Publication Data
US 2007/0059814 A1    Mar. 15, 2007

Related U.S. Application Data

(60) Provisional application No. 60/496,552, filed on Aug. 20, 2003, provisional application No. 60/548,201, filed on Feb. 27, 2004.

(51) Int. Cl.
*C12Q 1/68* (2006.01)
*C12P 19/34* (2006.01)
*C07H 21/04* (2006.01)

(52) U.S. Cl. .......................... 435/6; 435/91.2; 435/91.5; 435/91.51; 536/23.5

(58) Field of Classification Search .................. None
See application file for complete search history.

(56) References Cited

FOREIGN PATENT DOCUMENTS

| WO | WO 01/23426 A2 | 4/2001 |
|----|----------------|--------|
| WO | WO 02/079411 A2 | 10/2002 |
| WO | WO 03/032813 A2 | 4/2003 |
| WO | WO 2008/102557 A1 | 8/2008 |
| WO | WO 2008128043 A2 * | 10/2008 |

OTHER PUBLICATIONS

Wiesener, M.S. et al. Cancer Research 61:5215-5222 (Jul. 2001).*
Zhang, et al., "Foreign Medical Sciences (section of Clinical Biochemistry and Laboratory Medicine)," 2003, vol. 24(4): pp. 199-200.
Denko, Nicholas, et al.; "Epigenetic Regulation of Gene Expression in Cervical Cancer Cells by the Tumor Microenvironment;" *Clinical Cancer Research*; Feb. 2000; pp. 480-487; 6:2.
Togashi, A., et al.; "Hypoxia-Inducible Protein 2 (*HIG2*), a Novel Diagnostic Marker for Renal Cell Carcinoma and Potential Target for Molecular Therapy;" *The Journal of Urology*; Apr. 2006; p. 1272; 175:4.

(Continued)

*Primary Examiner*—Diana B Johannsen
(74) *Attorney, Agent, or Firm*—Townsend and Townsend and Crew LLP

(57) ABSTRACT

The present invention provides a method for inhibiting growth of a cancer cell, particularly a renal cell carcinoma, by contacting the cell with a composition composed of an HIG2 siRNA or HIG2 antibody. Methods of diagnosing renal cell cancer are also provided within the present invention.

7 Claims, 14 Drawing Sheets

OTHER PUBLICATIONS

Boer, Judith M. et al.; "Identification and classification of differentially expressed genes in renal cell carcinoma by expression profiling on a global human 31,500-element cDNA array"; *Genome Research* 11:1861-1870 (2001).

Huber, W. et al.; "Five outstanding research communications 2002"; *Verh. Dtsch. Ges. Path.* 86:153-164 (2002).

Jiang, Yide et al.; "Gene expression profiling in a renal cell carcinoma cell line: Dissecting VHL and hypoxia-dependent pathways"; *Molecular Cancer Research* 1:453-462 (Apr. 2003).

Moch, H. et al.; "Identification of potential prognostic parameters for renal cell carcinoma by tissue microarray analysis and cDNA microarray screening"; *Verh. Dtsch. Ges. Path.* 83:225-232 (1999).

Nishie, Akihiro et al.; "High expression of the *Cap43* gene in infiltrating macrophages of human renal cell carcinomas"; *Clinical Cancer Research* 7:2145-2151 (Jul. 2001).

Oudard, Stephane et al.; "Expression of genes involved in chemoresistance, proliferation and apoptosis in clinical samples of renal cell carcinoma and correlation with clinical outcome"; *Anticancer Research* 22:121-128 (2002).

Petros, John A. et al.; "cDNA microarray gene expression profiles of papillary renal cell carcinoma"; *Journal of Urology* 167(4 Suppl):126-127 (505) (2002) and *Annual Meeting of the American Urology Association, Inc.*; Orlando, Florida, May 25-30, 2002.

Shiina, Hiroaki et al.; "The human *T-cell factor-4* gene splicing isoforms, Wnt signal pathway, and apoptosis in renal cell carcinoma"; *Clinical Cancer Research* 9:2121-2132 (Jun. 2003).

Skubitz, Keith M. and Amy P. N. Skubitz; "Differential gene expression in renal-cell cancer"; *J. Lab. Clin. Med.* 140:52-64 (2002).

Stassar, M.J.J.G. et al.; "Identification of human renal cell carcinoma associated genes by suppression subtractive hybridization"; *British Journal of Cancer* 85(9):1372-1382 (2001).

Takahashi, Masayuki et al.; "Gene expression profiling of clear cell renal cell carcinoma: Gene identification and prognostic classification"; *PNAS* 98(17):9754-9759 (Aug. 14, 2001).

Jiang, Y., et al., "Gene Expression Profiling in a Renal Cell Carcinoma Cell Line: Dissecting VHL and Hypoxia-Dependent Pathways," *Molecular Cancer Research*, vol. 1(6), pp. 453-462 (Apr. 2003).

Latif, F., et al., "Identification of the von Hippel-Lindau Disease Tumor Suppressor Gene," *Science*, vol. 260(5112), pp. 1317-1320 (May 28, 1993).

Togashi, A., et al., "Hypoxia-Inducible Protein 2 (HIG2), a Novel Diagnostic Marker for Renal Cell Carcinoma and Potential Target for Molecular Therapy," *Cancer Res.*, vol. 65(11), pp. 4817-4826 (Jun. 1, 2005).

Togashi, A., et al., "Screening for novel therapeutic target and tumor marker of renal cell carcinoma using cDNA microarray," *Proceedings of the 62nd Annual Meeting of the Japanese Cancer Association*, p. 216, Abstract No. 3002-OA (Aug. 25, 2003).

Togashi, A., et al., "Identification of novel therapeutic target and tumor marker for renal cell carcinoma," *Proceedings of the 63rd Annual Meeting of the Japanese Cancer Association*, 95 (Supplement), p. 215, Abstract No. W-174 (Aug. 25, 2004).

Togashi, et al., "A novel potential molecular target for treatment of renal cell carcinoma (RCC)," *Proceedings of the 95th Annual Meeting of the American Association for Cancer Research*, vol. 45, pp. 481-482, Abstract No. 2093 (Mar. 2004).

\* cited by examiner

A

B

C

Fig. 3-1
A
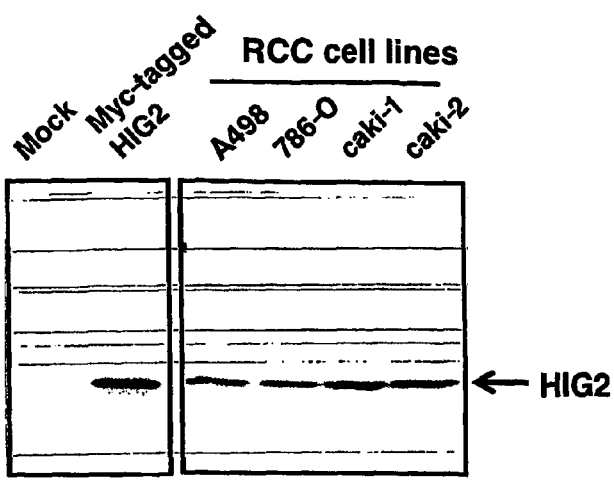
B
C
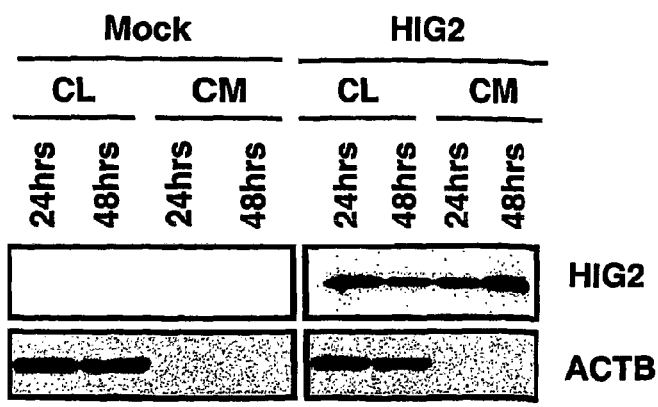

E heart liver lung spinal cord pancreas prostate

A

B

C

Fig. 5-1
A caki-1
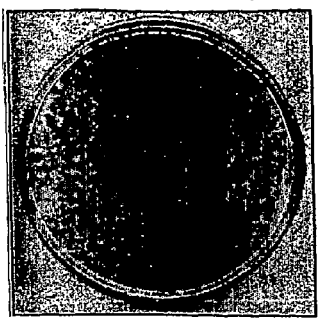
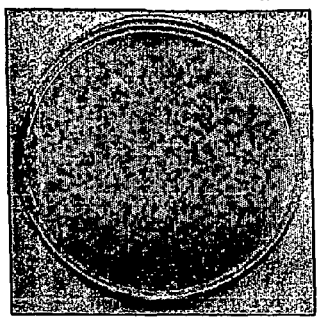
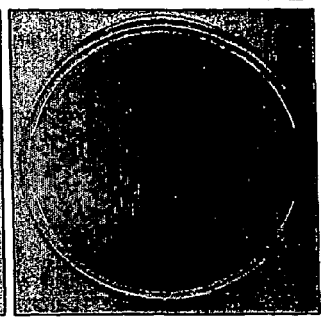
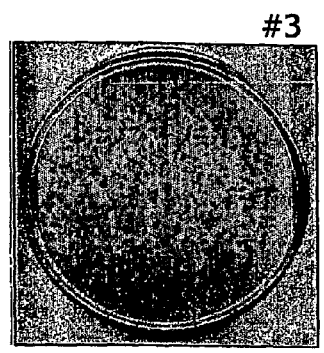
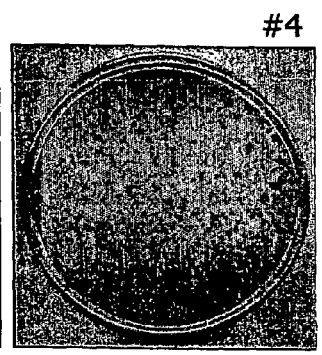
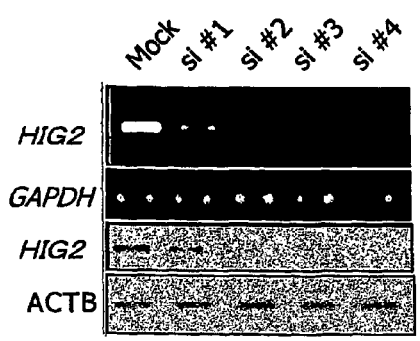
B caki-2
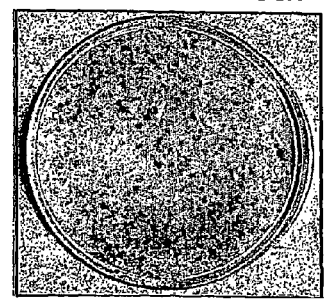
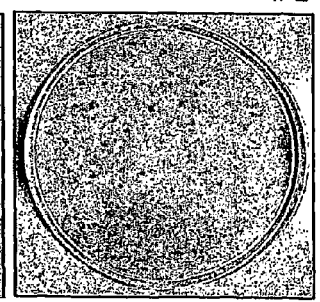
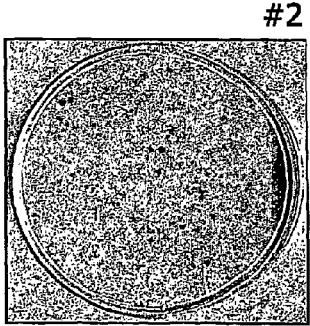
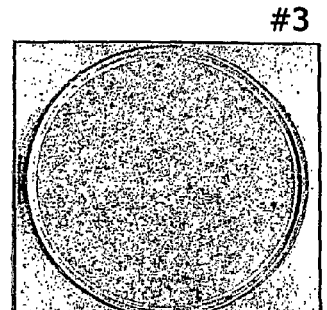
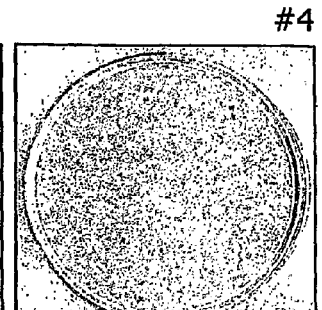
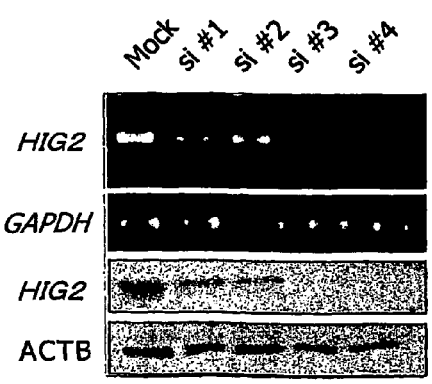

A

B

SEQUENCE LISTING

<160> NUMBER OF SEQ ID NOS: 101

<210> SEQ ID NO 1
<211> LENGTH: 1372
<212> TYPE: DNA
<213> ORGANISM: Homo sapiens
<220> FEATURE:
<221> NAME/KEY: CDS
<222> LOCATION: (206)..(397)

<400> SEQUENCE: 1
gcacgagggc gcttttgtct ccggtgagtt ttgtggcggg aagcttctgc gctggtgctt      60
agtaaccgac tttcctccgg actcctgcac gacctgctcc tacagccggc gatccactcc     120
cggctgttcc cccggagggt ccagaggcct ttcagaagga gaaggcagct ctgtttctct     180
gcagaggagt agggtccttt cagcc atg aag cat gtg ttg aac ctc tac ctg      232
                              Met Lys His Val Leu Asn Leu Tyr Leu
                                1               5

-continued

| | |
|---|---|
| tta ggt gtg gta ctg acc cta ctc tcc atc ttc gtt aga gtg atg gag<br>Leu Gly Val Val Leu Thr Leu Leu Ser Ile Phe Val Arg Val Met Glu<br>10                  15                20                25 | 280 |
| tcc cta gaa ggc tta cta gag agc cca tcg cct ggg acc tcc tgg acc<br>Ser Leu Glu Gly Leu Leu Glu Ser Pro Ser Pro Gly Thr Ser Trp Thr<br>                30                35                40 | 328 |
| acc aga agc caa cta gcc aac aca gag ccc acc aag ggc ctt cca gac<br>Thr Arg Ser Gln Leu Ala Asn Thr Glu Pro Thr Lys Gly Leu Pro Asp<br>45                  50                55 | 376 |
| cat cca tcc aga agc atg tga taagacctcc ttccatactg gccatatttt<br>His Pro Ser Arg Ser Met<br>           60 | 427 |
| ggaacactga cctagacatg tccagatggg agtcccattc ctagcagaca agctgagcac | 487 |
| cgttgtaacc agagaactat tactaggcct tgaagaacct gtctaactgg atgctcattg | 547 |
| cctgggcaag gcctgtttag gccggttgcg gtggctcatg cctgtaatcc tagcactttg | 607 |
| ggaggctgag gtgggtggat cacctgaggt caggagttcg agaccagcct cgccaacatg | 667 |
| gcgaaacccc atctctacta aaaatacaaa agttagctgg gtgtggtggc agaggcctgt | 727 |
| aatcccagtt ccttgggagg ctgaggcggg agaattgctt gaacccgggg acggaggttg | 787 |
| cagtgaaccg agatcgcact gctgtaccca gcctgggcca cagtgcaaga ctccatctca | 847 |
| aaaaaaaaa gaaagaaaaa agcctgttta atgcacaggt gtgagtggat tgcttatggc | 907 |
| tatgagatag gttgatctcg cccttacccc ggggtctggt gtatgctgtg ctttcctcag | 967 |
| cagtatggct ctgacatctc ttagatgtcc caacttcagc tgttgggaga tggtgatatt | 1027 |
| ttcaaccta cttcctaaac atctgtctgg ggttcctta gtcttgaatg tcttatgctc | 1087 |
| aattatttgg tgttgagcct ctcttccaca agagctcctc catgtttgga tagcagttga | 1147 |
| agaggttgtg tgggtgggct gttgggagtg aggatggagt gttcagtgcc catttctcat | 1207 |
| tttacatttt aaagtcgttc ctccaacata gtgtgtattg gtctgaaggg ggtggtggga | 1267 |
| tgccaaagcc tgctcaagtt atggacattg tggccaccat gtggcttaaa tgattttttc | 1327 |
| taactaataa agtggaatat atatttcaaa aaaaaaaaaa aaaaa | 1372 |

<210> SEQ ID NO 2
<211> LENGTH: 63
<212> TYPE: PRT
<213> ORGANISM: Homo sapiens
<220> FEATURE:
<223> OTHER INFORMATION: protein sequence

<400> SEQUENCE: 2

Met Lys His Val Leu Asn Leu Tyr Leu Leu Gly Val Val Leu Thr Leu
1               5                     10                    15

Leu Ser Ile Phe Val Arg Val Met Glu Ser Leu Glu Gly Leu Leu Glu
                  20                    25                    30

Ser Pro Ser Pro Gly Thr Ser Trp Thr Thr Arg Ser Gln Leu Ala Asn
                35                    40                    45

Thr Glu Pro Thr Lys Gly Leu Pro Asp His Pro Ser Arg Ser Met
50                  55                  60

<210> SEQ ID NO 3
<211> LENGTH: 20
<212> TYPE: DNA
<213> ORGANISM: Artificial sequence
<220> FEATURE:
<223> OTHER INFORMATION: an artificial synthesized primer sequence for
    RT-PCR

```
<400> SEQUENCE: 3
tggagcctaa aatggggaat                                                  20

<210> SEQ ID NO 4
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 4
aggtgcgttg aacccatatt                                                  20

<210> SEQ ID NO 5
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 5
tgccctttca cacacacttt                                                  20

<210> SEQ ID NO 6
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 6
ggagttgggg gagaaggagt                                                  20

<210> SEQ ID NO 7
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 7
tgtccaggag acagagctga                                                  20

<210> SEQ ID NO 8
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 8
gagcagtctc agggacatgg                                                  20

<210> SEQ ID NO 9
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 9
tgctttctgc atttggtgtt                                          20

<210> SEQ ID NO 10
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 10
gaattttggg gtgtttccaa                                          20

<210> SEQ ID NO 11
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 11
cagctggaga ctggctctct                                          20

<210> SEQ ID NO 12
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 12
cagtttcaac aggtaaggcg ata                                      23

<210> SEQ ID NO 13
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 13
ccagcattta tggcaaatgg                                          20

<210> SEQ ID NO 14
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 14
tgaccctcca aatgtaccaa a                                        21

<210> SEQ ID NO 15
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 15
cttctgcgtg acaactgagg                                              20

<210> SEQ ID NO 16
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 16
ctcccaagca taaaacagca                                              20

<210> SEQ ID NO 17
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 17
gcgacaagtc agacctagcc                                              20

<210> SEQ ID NO 18
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 18
tctaactgcc tcccaggaca                                              20

<210> SEQ ID NO 19
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 19
gaggaccttg actgggttca                                              20

<210> SEQ ID NO 20
<211> LENGTH: 22
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 20
caggtcaaga gaccctttct tc                                           22

<210> SEQ ID NO 21
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 21
gggacatggg gagcttagat                                         20

<210> SEQ ID NO 22
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 22
caaaaaggtg caccaaaaca                                         20

<210> SEQ ID NO 23
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 23
gagcacatcc tacgcacaag                                         20

<210> SEQ ID NO 24
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 24
gctaaatttg gggcaatttg t                                       21

<210> SEQ ID NO 25
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 25
tggcaaaatt ctgatgcaaa                                         20

<210> SEQ ID NO 26
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 26
ttgggctttt tggaaaattg                                         20

<210> SEQ ID NO 27
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 27
agtttggcag gcatgaagag                                              20

<210> SEQ ID NO 28
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 28
cgggatctgc acacatcttt                                              20

<210> SEQ ID NO 29
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 29
cccaaaatgg gtgtatctgg                                              20

<210> SEQ ID NO 30
<211> LENGTH: 24
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 30
ggttctgagc aacctctata actg                                         24

<210> SEQ ID NO 31
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 31
aagcccaact ttgatatagc ctg                                          23

<210> SEQ ID NO 32
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 32
ctttattggt gtgtttgagc tgg                                          23

<210> SEQ ID NO 33
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

<400> SEQUENCE: 33
tagtctgctg gctgactgga                                                    20

<210> SEQ ID NO 34
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 34
acaagaatga aaaaggccac a                                                  21

<210> SEQ ID NO 35
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 35
tcaatcccag aaggaagctg                                                    20

<210> SEQ ID NO 36
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 36
aagctatggc cgtgaaaatg                                                    20

<210> SEQ ID NO 37
<211> LENGTH: 24
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 37
catatctgtc tcattctgcc tttt                                               24

<210> SEQ ID NO 38
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 38
aacaggccca tattacccct                                                    20

<210> SEQ ID NO 39
<211> LENGTH: 22
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 39
agcgtgactt tcagttttga ct                                              22

<210> SEQ ID NO 40
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 40
aatgcaactg ttcgttgtgt g                                               21

<210> SEQ ID NO 41
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 41
tccaattgtc tgagctgtcg                                                 20

<210> SEQ ID NO 42
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 42
aactcccagt caccctgttt t                                               21

<210> SEQ ID NO 43
<211> LENGTH: 25
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 43
tttcagatcg gtcactgata gtatg                                           25

<210> SEQ ID NO 44
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 44
gtgaaatctc aaggataagg agg                                             23

<210> SEQ ID NO 45
<211> LENGTH: 19
<212> TYPE: DNA
<213> ORGANISM: Artificial sequence
<220> FEATURE:
<223> OTHER INFORMATION: an artificially synthesized primer sequence for
      RT-PCR

```
<400> SEQUENCE: 45
tcgtcaacca gcagagctt                                                      19

<210> SEQ ID NO 46
<211> LENGTH: 18
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 46
ccgcgtagtt catctgcc                                                       18

<210> SEQ ID NO 47
<211> LENGTH: 22
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 47
tgtctcctga ccagtgtcag tt                                                  22

<210> SEQ ID NO 48
<211> LENGTH: 22
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 48
tcacacttga ccatgagtgt tg                                                  22

<210> SEQ ID NO 49
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 49
accctcagcc aagattggta                                                     20

<210> SEQ ID NO 50
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 50
tgcctttatt tgtccccttg                                                     20

<210> SEQ ID NO 51
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 51
tgaacgcaca tgacatagca                                              20

<210> SEQ ID NO 52
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 52
ttttcaaatg gcagtttctg a                                            21

<210> SEQ ID NO 53
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 53
cctccaagct cctctgactg                                              20

<210> SEQ ID NO 54
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 54
tgaaaagcag gtgagtctgg t                                            21

<210> SEQ ID NO 55
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 55
accatcaagg aagcagcaag                                              20

<210> SEQ ID NO 56
<211> LENGTH: 21
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 56
aacagctccc tttttcgtag c                                            21

<210> SEQ ID NO 57
<211> LENGTH: 20
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 57
gtagggtctg cctgttggaa                                        20

<210> SEQ ID NO 58
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 58
actaaatgcc aaggggact                                         20

<210> SEQ ID NO 59
<211> LENGTH: 20
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 59
ctcttgacct gtcccctctg                                        20

<210> SEQ ID NO 60
<211> LENGTH: 25
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 60
cgttgataac attactcaag tcaca                                  25

<210> SEQ ID NO 61
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 61
agataggttg atctcgccct tac                                    23

<210> SEQ ID NO 62
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 62
acacctcttc aactgctatc caa                                    23

<210> SEQ ID NO 63
<211> LENGTH: 21
<212> TYPE: DNA
<213> ORGANISM: Artificial sequence
<220> FEATURE:
<223> OTHER INFORMATION: an artificially synthesized primer sequence for
      RT-PCR
```

```
<400> SEQUENCE: 63
gatggattgc agagagacct g                                              21

<210> SEQ ID NO 64
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 64
tcatacacac acaaaccacc agt                                            23

<210> SEQ ID NO 65
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 65
cgatacagat atgttcggtg atg                                            23

<210> SEQ ID NO 66
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 66
cctccattct tcatctctca atg                                            23

<210> SEQ ID NO 67
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 67
cttgggtctg taacaaagca ttc                                            23

<210> SEQ ID NO 68
<211> LENGTH: 23
<212> TYPE: DNA
<213> ORGANISM: Artificial sequence
<220> FEATURE:
<223> OTHER INFORMATION: an artificially synthesized primer sequence for
      RT-PCR

<400> SEQUENCE: 68
aaggattatg aggaggttgg tgt                                            23

<210> SEQ ID NO 69
<211> LENGTH: 21
<212> TYPE: DNA
<213> ORGANISM: Artificial sequence
<220> FEATURE:
<223> OTHER INFORMATION: an artificially synthesized primer sequence
```

```
<400> SEQUENCE: 69
tttctctgca gaggagtagg g                                              21

<210> SEQ ID NO 70
<211> LENGTH: 19
<212> TYPE: DNA
<213> ORGANISM: Artificial sequence
<220> FEATURE:
<223> OTHER INFORMATION: an artificially synthesized primer sequence

<400> SEQUENCE: 70
catgcttctg gatggatgg                                                 19

<210> SEQ ID NO 71
<211> LENGTH: 22
<212> TYPE: DNA
<213> ORGANISM: Artificial sequence
<220> FEATURE:
<223> OTHER INFORMATION: an artificially synthesized primer sequence

<400> SEQUENCE: 71
tggtagccaa gtgcaggtta ta                                             22

<210> SEQ ID NO 72
<211> LENGTH: 22
<212> TYPE: DNA
<213> ORGANISM: Artificial sequence
<220> FEATURE:
<223> OTHER INFORMATION: an artificially synthesized primer sequence

<400> SEQUENCE: 72
ccaaagggtt tctgcagttt ca                                             22

<210> SEQ ID NO 73
<211> LENGTH: 30
<212> TYPE: DNA
<213> ORGANISM: Artificial sequence
<220> FEATURE:
<223> OTHER INFORMATION: an artificially synthesized primer sequence

<400> SEQUENCE: 73
tgcggatcca gagcagattg tactgagagt                                     30

<210> SEQ ID NO 74
<211> LENGTH: 29
<212> TYPE: DNA
<213> ORGANISM: Artificial sequence
<220> FEATURE:
<223> OTHER INFORMATION: an artificially synthesized primer sequence

<400> SEQUENCE: 74
ctctatctcg agtgaggcgg aaagaacca                                      29

<210> SEQ ID NO 75
<211> LENGTH: 47
<212> TYPE: DNA
<213> ORGANISM: Artificial sequence
<220> FEATURE:
<223> OTHER INFORMATION: an artificially synthesized primer sequence

<400> SEQUENCE: 75
tttaagcttg aagaccattt ttggaaaaaa aaaaaaaaa aaaaaac                   47
```

```
<210> SEQ ID NO 76
<211> LENGTH: 34
<212> TYPE: DNA
<213> ORGANISM: Artificial sequence
<220> FEATURE:
<223> OTHER INFORMATION: an artificially synthesized primer sequence

<400> SEQUENCE: 76
tttaagcttg aagacatggg aaagagtggt ctca                           34

<210> SEQ ID NO 77
<211> LENGTH: 19
<212> TYPE: DNA
<213> ORGANISM: Artificial sequence
<220> FEATURE:
<223> OTHER INFORMATION: an artificially synthesized primer sequence

<400> SEQUENCE: 77
gcatgtgata agacctcct                                            19

<210> SEQ ID NO 78
<211> LENGTH: 19
<212> TYPE: DNA
<213> ORGANISM: Artificial sequence
<220> FEATURE:
<223> OTHER INFORMATION: an artificially synthesized primer sequence

<400> SEQUENCE: 78
cactgaccta gacatgtcc                                            19

<210> SEQ ID NO 79
<211> LENGTH: 19
<212> TYPE: DNA
<213> ORGANISM: Artificial sequence
<220> FEATURE:
<223> OTHER INFORMATION: an artificially synthesized primer sequence

<400> SEQUENCE: 79
gaacctgtct aactggatg                                            19

<210> SEQ ID NO 80
<211> LENGTH: 19
<212> TYPE: DNA
<213> ORGANISM: Artificial sequence
<220> FEATURE:
<223> OTHER INFORMATION: an artificially synthesized primer sequence

<400> SEQUENCE: 80
cctgtctaac tggatgctc                                            19

<210> SEQ ID NO 81
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 81
tcccgaagca gcacgacttc ttcttcaaga gagaagaagt cgtgctgctt c        51

<210> SEQ ID NO 82
<211> LENGTH: 51
<212> TYPE: DNA
<213> ORGANISM: Artificial sequence
```

```
<220> FEATURE:
<223> OTHER INFORMATION: an artificially synthesized oligonucleotide
      sequence for siRNA

<400> SEQUENCE: 82
aaaagaagca gcacgacttc ttctctcttg aagaagaagt cgtgctgctt c         51

<210> SEQ ID NO 83
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 83
tcccgcatgt gataagacct cctttcaaga gaaggaggtc ttatcacatg c          51

<210> SEQ ID NO 84
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 84
aaaagcatgt gataagacct ccttctcttg aaaggaggtc ttatcacatg c          51

<210> SEQ ID NO 85
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 85
tccccactga cctagacatg tccttcaaga gaggacatgt ctaggtcagt g          51

<210> SEQ ID NO 86
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 86
aaaacactga cctagacatg tcctctcttg aaggacatgt ctaggtcagt g          51

<210> SEQ ID NO 87
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 87
tcccgaacct gtctaactgg atgttcaaga gacatccagt tagacaggtt c          51

<210> SEQ ID NO 88
<211> LENGTH: 51
<212> TYPE: DNA
<213> ORGANISM: Artificial sequence
```

```
<220> FEATURE:
<223> OTHER INFORMATION: an artificially synthesized oligonucleotide
      sequence for siRNA

<400> SEQUENCE: 88
aaaagaacct gtctaactgg atgtctcttg aacatccagt tagacaggtt c        51

<210> SEQ ID NO 89
<211> LENGTH: 51
<212> TYPE: DNA
<213> ORGANISM: Artificial sequence
<220> FEATURE:
<223> OTHER INFORMATION: an artificially synthesized oligonucleotide
      sequence for siRNA

<400> SEQUENCE: 89
tccccctgtc taactggatg ctcttcaaga gagagcatcc agttagacag g         51

<210> SEQ ID NO 90
<211> LENGTH: 51
<212> TYPE: DNA
<213> ORGANISM: Artificial sequence
<220> FEATURE:
<223> OTHER INFORMATION: an artificially synthesized oligonucleotide s
      equence for siRNA

<400> SEQUENCE: 90
aaaacctgtc taactggatg ctctctcttg aagagcatcc agttagacag g         51

<210> SEQ ID NO 91
<211> LENGTH: 14
<212> TYPE: PRT
<213> ORGANISM: Artificial sequence
<220> FEATURE:
<223> OTHER INFORMATION: an artificially synthesized peptide sequence

<400> SEQUENCE: 91

Glu Pro Thr Lys Gly Leu Pro Asp His Pro Ser Arg Ser Met
1               5                   10

<210> SEQ ID NO 92
<211> LENGTH: 3
<212> TYPE: RNA
<213> ORGANISM: Artificial sequence
<220> FEATURE:
<223> OTHER INFORMATION: An artificially synthesized oligonucleotide
      sequence

<400> SEQUENCE: 92 ccc                                                              3

<210> SEQ ID NO 93
<211> LENGTH: 5
<212> TYPE: RNA
<213> ORGANISM: Artificial sequence
<220> FEATURE:
<223> OTHER INFORMATION: An artificially synthesized oligonucleotide
      sequence

<400> SEQUENCE: 93 ccacc                                                            5

<210> SEQ ID NO 94
<211> LENGTH: 7
<212> TYPE: RNA
<213> ORGANISM: Artificial sequence
```

```
<220> FEATURE:
<223> OTHER INFORMATION: An artificially synthesized oligonucleotide
      sequence

<400> SEQUENCE: 94 ccacacc                                                                  7

<210> SEQ ID NO 95
<211> LENGTH: 4
<212> TYPE: RNA
<213> ORGANISM: Artificial sequence
<220> FEATURE:
<223> OTHER INFORMATION: An artificially synthesized oligonucleotide
      sequence

<400> SEQUENCE: 95 uucg                                                                     4

<210> SEQ ID NO 96
<211> LENGTH: 9
<212> TYPE: RNA
<213> ORGANISM: Artificial sequence
<220> FEATURE:
<223> OTHER INFORMATION: An artificially synthesized oligonucleotide
      sequence

<400> SEQUENCE: 96 uucaagaga                                                                9

<210> SEQ ID NO 97
<211> LENGTH: 9
<212> TYPE: DNA
<213> ORGANISM: Artificial sequence
<220> FEATURE:
<223> OTHER INFORMATION: An artificially synthesized oligonucleotide
      sequence

<400> SEQUENCE: 97 ttcaagaga                                                                9

<210> SEQ ID NO 98
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 98
aggaggtctt atcacatgc                                                    19

<210> SEQ ID NO 99
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 99
ggacatgtct aggtcagtg                                                    19

<210> SEQ ID NO 100
<211> LENGTH: 19
<212> TYPE: DNA
<213> ORGANISM: Artificial sequence
```

```
<220> FEATURE:
<223> OTHER INFORMATION: An artificially synthesized oligonucleotide
      sequence

<400> SEQUENCE: 100
catccagtta gacaggttc                                                      19

<210> SEQ ID NO 101
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 101
gagcatccag ttagacagg                                                      19
```

HYPOXIA-INDUCIBLE PROTEIN 2 (HIG2), A DIAGNOSTIC MARKER FOR CLEAR CELL RENAL CELL CARCINOMA

This application claims the benefit of U.S. Provisional Application Ser. No. 60/496,552 filed Aug. 20, 2003, and U.S. Provisional Application Ser. No. 60/548,201 filed Feb. 27, 2004, the contents of which are hereby incorporated by reference in their entirety.

TECHNICAL FIELD

The present invention relates to genes and proteins that are differentially expressed in renal cell carcinoma and methods of using same to diagnose and treat renal cell carcinoma.

BACKGROUND OF TH INVENTION

Renal cell carcinoma (RCC) is the third most common malignancy of the genitourinary system and corresponds to 2-3% of all human malignancies. Surgical resection is the most effective treatment for patients with localized RCC tumors, but such treatment for patients with advanced-stage RCC is not satisfactory. Although some biomedical therapies have been reported to show ~20% response rate, they often cause severe adverse reactions and do not generally improve patients' survival. Among patients who have surgical treatment, approximately 25-30% relapse after surgery (Ljungberg B., Alamdari F. I., Rasmuson T. & Roos G. Follow-up guidelines for nonmetastatic renal cell carcinoma based on the occurrence of metastases after radical nephrectomy. *BJU Int.* 84, 405-411 (1999); Levy D A., Slaton J W., Swanson D A. & Dinney C P. Stage specific guidelines for surveillance after radical nephrectomy for local renal cell carcinoma. *J Urol.* 159, 1163-1167 (1998)). Tumor stage and surgical respectability are the most important prognostic factors for RCC; however, to date, little is known of the underlying molecular mechanisms that influence this variety in prognoses.

RCC tumors can be subdivided on the basis of histological features into clear cell (80%), papillary (~10%), chromophobe (<5%), granular, spindle and cyst-associated carcinomas (5-15%). Each of these histological subtypes shows unique clinical behavior, with clear-cell and granular types tending to show more aggressive clinical phenotypes. Studies designed to reveal mechanisms of carcinogenesis have already facilitated the identification of molecular targets for certain anti-tumor agents. For example, inhibitors of farnesyltransferase (FTIs), which were originally developed to inhibit the growth-signaling pathway related to Ras, whose activation depends on post-translational farnesylation, have been shown to be effective in treating Ras-dependent tumors in animal models (He et al., Cell 99:335-45 (1999)). Similarly, clinical trials on humans using a combination of anti-cancer drugs and the anti-HER2 monoclonal antibody, trastuzumab, with the aim of antagonizing the proto-oncogene receptor HER2/neu, have resulted in improved clinical response and overall survival of breast-cancer patients (Lin et al., Cancer Res 61:6345-9 (2001)). Finally, a tyrosine kinase inhibitor, STI-571, which selectively inactivates bcr-abl fusion proteins, has been developed to treat chronic myelogenous leukemias, wherein constitutive activation of bcr-abl tyrosine kinase plays a crucial role in the transformation of leukocytes. Agents of these kinds are designed to suppress oncogenic activity of specific gene products (Fujita et al., Cancer Res 61:7722-6 (2001)). Accordingly, it is apparent that gene products commonly up-regulated in cancerous cells may serve as potential targets for developing novel anti-cancer agents.

It has been further demonstrated that CD8+ cytotoxic T lymphocytes (CTLs) recognize epitope peptides derived from tumor-associated antigens (TAAs) presented on the MHC Class I molecule, and lyse tumor cells. Since the discovery of the MAGE family as the first examples of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the newly discovered TAAs are currently undergoing clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products demonstrated to be specifically over-expressed in tumor cells have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenbeg et al., Nature Med 4: 321-7 (1998); Mukherji et al., Proc Natl Acad Sci USA 92: 8078-82 (1995); Hu et al., Cancer Res 56: 2479-83 (1996)), only limited number of candidate TAAs for the treatment of adenocarcinomas, including colorectal cancer, are currently available. TAAs abundantly expressed in cancer cells yet whose expression is restricted to cancer cells would be promising candidates as immunotherapeutic targets. Further, identification of new TAAs inducing potent and specific antitumor immune responses is expected to encourage clinical use of peptide vaccination strategies for various types of cancer (Boon and can der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-5 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both HLA-A24 and HLA-A0201 are popular HLA alleles in the Japanese, as well as the Caucasian populations (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Hictocompatibility Workshop and Conference Oxford University Press, Oxford, 1065 (1992); Williams et al., Tissue Antigen 49: 129 (1997)). Thus, antigenic peptides of carcinomas presented by these HLAs may be especially useful for the treatment of carcinomas among Japanese and Caucasians. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

A hereditary cancer syndrome that sometimes involves the kidney, von Hippel-Lindau disease, results from germline mutations in the VHL gene (Latif F., Tory K., Gnarra J., Yao M., Duh F M., Orcutt M L., Stackhouse T., Kuzmin I., Modi W., Geil L., et al. Identification of the von Hippel-Lindau disease tumor suppressor gene. *Science.* 260, 1317-20 (1993)). VHL is often inactivated in RCCs as well. Under physiological conditions, mutations or deletions of VHL lead to aberrant accumulation of the HIF1 protein due to dysfunction of ubiquitination machinery; in turn, accumulated HIF1 evokes the constitutive expression of downstream genes associated with growth and development of tumor cells. For example, Denko et al. demonstrated that expression of HIG2 is regulated by HIF1 under the hypoxic condition using the cells established from HIF1 deficient mouse (Denko N. et al., Epigenetic regulation of gene expression in cervical cancer cells by the tumor microenvironment. *Clin Cancer Res.* 6, 480-487 (2000) and on the worldwide web at 171.65.6.67/Hypoxia/outline%20for%20hig2.htm). HIF1 is composed of two subunits, HIF1α and HIF1β3. HIF1α is the oxygen-regulated component that determines HIF1 activity, and is rapidly degraded via ubiquitin-proteasome pathway under normoxic conditions.

To date, some genes that might be useful for prediction of prognosis or for classification of RCCs have been identified by cluster analysis (Takahashi M., Rhodes D R, Furge K A., Kanayama H., Kagawa S., Haab B B., Teh B T. Gene expression profiling of clear cell renal cell carcinoma: gene identification and prognostic classification. *Proc Natl Acad. Sci.* 98, 9754-9759 (2001); Skubitz K M., Skubitz A P. Differential gene expression in renal-cell cancer. *J Lab Clin Med.* 140, 52-64 (2002)). In an effort to understand the carcinogenic mechanisms associated with RCC and identify potential targets for developing novel anti-cancer agents for RCC, the present inventors performed large scale analyses of gene expression profiles of tumors of the predominant type, clear cell carcinoma.

SUMMARY OF THE INVENTION

Accordingly, the present invention is involves the discovery of a pattern of gene expression correlated with renal cell carcinoma. The genes that are differentially expressed in renal cell carcinoma are collectively referred to herein as "RCCX nucleic acids" or "RCCX polynucleotides" and the corresponding encoded polypeptides are referred to as "RCCX polypeptides" or "RCCX proteins."

HIG2 is over-expressed in renal cell carcinoma as compared to normal, non-cancerous renal tissue and other normal tissues. Specifically, ELISA analyses of clinical materials obtained from RCC patients identified secretion of HIG2 protein in the plasma from RCC patients even at an early stage of tumor, whereas HIG2 protein not was detected in either normal healthy volunteers or chronic glomerulonephritis patients. HIG2 over-expression leads to an aberrant increase in renal cell proliferation and tumor formation. Accordingly, the present invention features methods of inhibiting cell growth by contacting a cell with a composition of an HIG2 small interfering RNA (siRNA). Alternatively, cell growth can be inhibited by contacting a cell with a composition of an HIG2 specific antibody or fragment thereof. The cell can be provided in vitro, in vivo or ex vivo. The subject can be a mammal, e.g., a human, non-human primate, mouse, rat, dog, cat, horse, or cow. The cell can be a cell of the genitourinary system, such as a renal cell. Alternatively, the cell can be a tumor cell (i.e., cancer cell), such as a carcinoma cell. For example, the cell can be a renal cell carcinoma cell, such as a clear cell. The phrase "inhibiting cell growth" encompasses treatment that results in cells that proliferate at a lower rate or have decreased viability as compared to untreated cells. Cell growth can be measured by proliferation assays known in the art.

The term "siRNA" refers to a double stranded RNA molecule that prevents translation of a target mRNA. Standard techniques for introducing an siRNA into a cell can be used, including those in which the DNA is a template from which RNA is transcribed. In the context of the present invention, the siRNA includes a sense HIG2 nucleic acid sequence, an anti-sense HIG2 nucleic acid sequence or both. The siRNA is preferably constructed such that a single transcript has both the sense and complementary antisense sequences from the target gene, e.g., a hairpin.

The term "HIG2 antibody" refers to a polyclonal or monoclonal antibody that has binding specificity for an HIG2 protein. The antibody can be an intact antibody. Alternatively, the antibody can be a fragment. Antibody fragments include, for example, Fab, F(ab')$_2$, or Fv fragments. In the context of the present invention, the antibody binds to an epitope in a hydrophilic domain, e.g., the C-terminal 14 residues of HIG2, EPTKGLPDHPSRSM (SEQ ID NO: 91). Alternatively, the antibody can bind to a hydrophobic domain of HIG2 or C-terminus of HIG2.

The method of the present invention can be used to alter gene expression a cell in which expression of HIG2 is up-regulated as a result of malignant transformation of the cells. Binding of an siRNA to an HIG2 transcript in a target cell results in reduction in HIG2 production by the cell. The length of the oligonucleotide is typically at least 10 nucleotides but can be as long as the naturally-occurring HIG2 transcript. Preferably, the oligonucleotide is 19-25 nucleotides in length. Most preferably, the oligonucleotide is less than 75, less than 50, or less than 25 nucleotides in length. For example, HIG2 siRNA oligonucleotides which inhibit HIG2 expression in mammalian cells include oligonucleotides containing SEQ ID NO: 77-80.

Alternatively, the method of the present invention can be used to alter HIG2 protein activity in a cell or tissue in which expression of HIG2 is up-regulated. In the context of the present invention, the phrase "biological activity of HIG2" generally refers to the promotion of cell proliferation. For example, contacting a cell, e.g., a renal cell, with HIG2 leads to an increase in cell proliferation. Conversely, binding of an HIG2 antibody to HIG2 results in a reduction in the cell proliferation promoting activity of native HIG2.

Also included in the invention are isolated nucleic acid molecules that include the nucleic acid sequences of SEQ ID NO: 77-80 or a nucleic acid molecule that is complementary to the nucleic acid sequences of SEQ ID NO: 77-80. As used herein, the term "complementary" refers to Watson-Crick or Hoogsteen base pairing between nucleotides units of a nucleic acid molecule, and the term "binding" refers to the physical or chemical interaction between two polypeptides or compounds or associated polypeptides or compounds or combinations thereof. In the context of the present invention, the nucleic acid molecule is preferably less than 1372 nucleotides in length. For example, the nucleic acid molecule can be less than 500, less than 200, or less than 75 nucleotides in length. Also included in the present invention are vectors containing one or more of the nucleic acids described herein, and cells containing such vectors.

The present invention further features a method of diagnosing or determining a predisposition to developing renal cell carcinoma in a subject, including the step of determining a level of expression of a renal cell carcinoma-associated gene in a patient-derived biological sample, such as a tissue sample or body fluid sample. The term "renal cell carcinoma" includes clear cell, papillary, chromophobe, granular, spindle and cyst-associated cell carcinoma. In the context of the present invention, a renal cell carcinoma-associated gene refers to a gene that is characterized by a level of expression which differs in a cell obtained from a renal cell carcinoma cell as compared to a normal cell. Herein, a "normal" cell is a cell obtained from renal tissue known not to be cancerous. A renal cell carcinoma-associated gene includes e.g., one or more of the RCCX 1-32 genes. An alteration, e.g., increase of the level of expression of the gene as compared to a normal control level of the gene indicates that the subject suffers from or is at risk of developing renal cell carcinoma. The method of the present invention is useful to detect early stage tumors, e.g., prior to detection of a mutation or deletion in a von Hippel-Lindau (VHL) gene or in the absence of such a mutation. For example, the method of the present invention can be used to detect malignant disease pre-stage I, stage I, stage II, as well as more advanced stages of malignancy.

The phrase "normal control level" refers to a level of gene expression detected in a normal, healthy individual or in a population of individuals known not to be suffering from renal cell carcinoma. A control level can be a single expression pattern derived from a single reference population or an expression pattern derived from a plurality of expression patterns. For example, in the context of the present invention, the control level can be a database of expression patterns from previously tested cells.

An increase in the level of any one of the RCCX 1-32 genes detected in a test sample as compared to a normal control level indicates that the subject (from which the sample was obtained) suffers from or is at risk of developing renal cell carcinoma.

Alternatively, expression of a panel of renal cell carcinoma-associated genes in the sample can be compared to a renal cell carcinoma reference level of the same panel of genes. In the context of the present invention, a "renal cell carcinoma reference level" refers to an expression profile of the renal cell carcinoma-associated genes found in a population suffering from renal cell carcinoma Gene expression can be increased by 10%, 25%, or 50% as compared to a normal control level. Alternately, gene expression can be increased 1, 2, 5 or more fold as compared to a normal control level. Expression is determined by detecting hybridization, e.g., on a chip or array, of a renal cell carcinoma-associated gene probe to a gene transcript or copy thereof of the patient-derived tissue sample.

The patient-derived tissue sample can be any tissue from a test subject, e.g., a patient known to or suspected of having renal cell carcinoma. For example, the tissue can comprise sputum, blood, serum, plasma, or a renal cell (e.g., biopsy sample obtained from the genitourinary system such as the kidney).

The present invention also provides a renal cell carcinoma reference expression profile of a gene expression level of two or more of the RCCX 1-32 genes.

The present invention further provides methods of identifying agents that inhibit the expression or activity of a renal cell carcinoma-associated gene, e.g., an RCCX 1-32 gene, including the step of contacting a test cell expressing a renal cell carcinoma-associated gene with a test agent and determining the subsequent expression level of the renal cell carcinoma-associated gene. The test cell can be a renal cell. A decrease in the level of an RCCX 1-32 gene in the presence of a tests agent as compared to a control level of the gene (e.g., in the absence of the test agent) indicates that the test agent is an inhibitor of the renal cell carcinoma-associated gene which can be used to reduce a symptom of renal cell carcinoma.

The present invention also includes vaccines and vaccination methods. For example, a method of treating or preventing RCC in a subject can be carried out by administering to the subject a vaccine containing a polypeptide encoded by an RCCX 1-32 gene or an immunologically active fragment such a polypeptide. In the context of the present invention, an immunologically active fragment is a polypeptide that is shorter in length than the full-length naturally-occurring protein yet which is capable of inducing an immune response. For example, in the context of the present invention, the immunologically active fragment should be at least 8 residues in length and capable of stimulating an immune cell such as a T cell or a B cell. Immune cell stimulation can be measured by detecting cell proliferation, elaboration of cytokines (e.g., IL-2), or production of an antibody.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Figure 1:
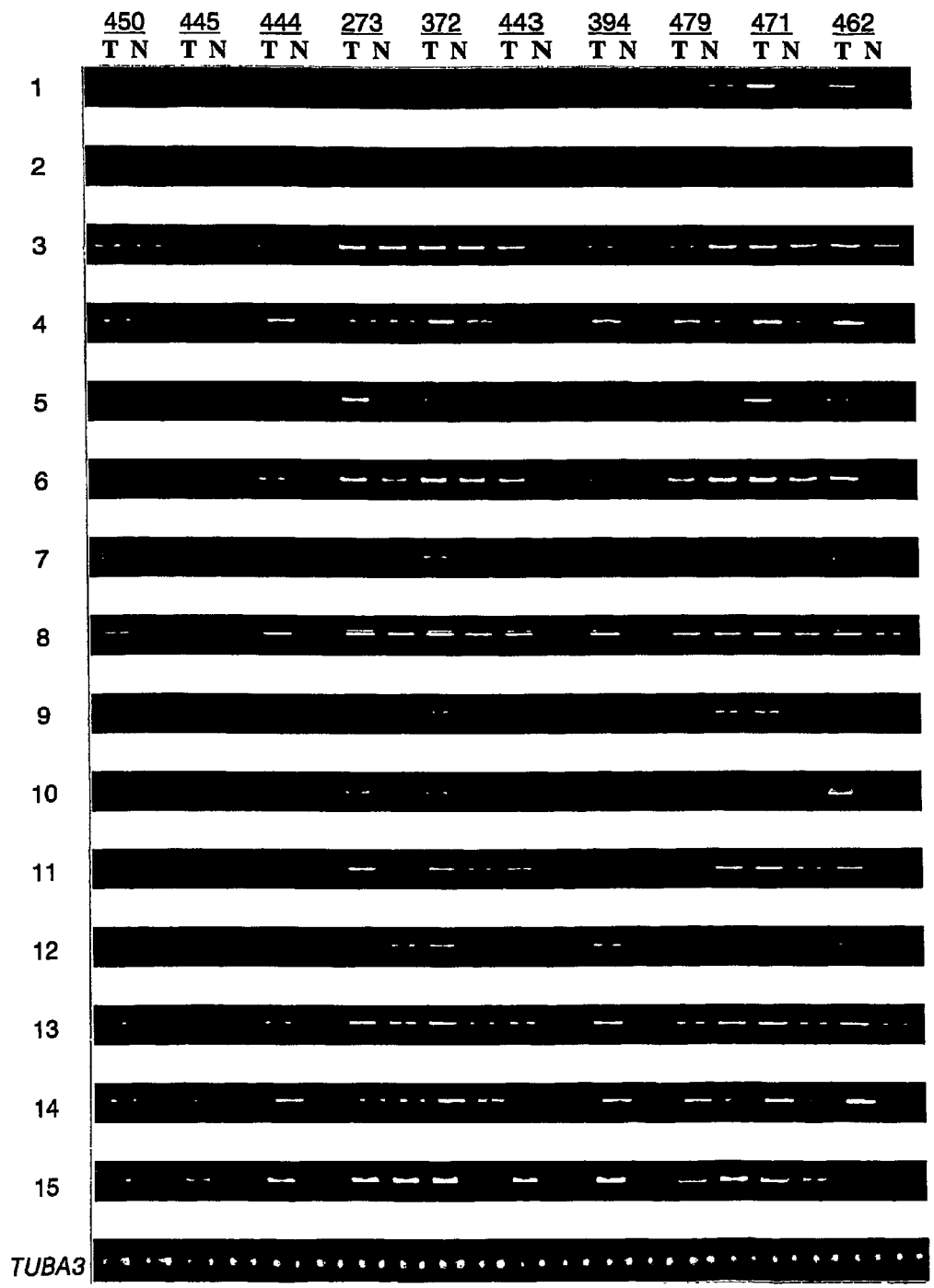
FIG. 1 is a photograph of a blot showing the expression of 32 genes up-regulated in renal cell carcinoma. Semi-quantitative RT-PCR confirmed the up-regulation.

The data described herein represents the expression analysis of genome-wide genes in renal cell carcinoma (RCC). Specifically, the present data provides comprehensive, genome-wide expression profiles of renal cell carcinoma obtained from measuring the expression of over 23,000 genes in clinical samples. The differentially expressed genes identified herein are used for diagnostic purposes and to develop gene targeted therapeutic approaches for inhibiting renal cell carcinoma.

cDNA microarray analysis was performed on over 23,000 genes and genes that were consistently and reliably over-expressed among renal cell carcinoma cancer patients were selected. Specifically, 32 genes were found to be over-expressed in more than 50% of the samples examined. In particular, hypoxia-inducible protein-2 (HIG2) was significantly over-expressed in 9 of 10 RCC cases examined. Subsequent semi-quantitative RT-PCR, northern blot and immunohistochemical analyses confirmed that HIG2 was significantly up-regulated in RCC cells, but not detected in any normal vital organ.

The present invention is based in part on the discovery that the gene encoding hypoxia-inducible protein-2 (HIG2), is over-expressed in renal cell carcinoma (RCC) as compared to non-cancerous kidney tissue. HIG2 was first identified as a gene induced by hypoxia (Denko N., Schindler C., Koong A., Laderoute K., Green C., Giaccia A. Epigenetic regulation of gene expression in cervical cancer cells by the tumor microenvironment. *Clin Cancer Res.* 6, 480-487 (2000)). The HIG2 cDNA is 1372 nucleotides in length (GENBANK Accession No. NM_013332; SEQ ID NO:1). The ORF, spanning residues 206-394, encodes a 63-amino acid protein and signal sequence at codon 1-21 predicted by Signal IP.

Exogenous expression of HIG2 in COS7 cells resulted in increased cell growth. In contrast, suppression of its expression with antisense S-oligonucleotides or through the neutralization of HIG2 protein activity with HIG2 specific polyclonal antibodies resulted in a growth inhibition of renal cells, e.g., renal carcinoma cells or embryonic kidney cells.

Accordingly, the present invention relates to a method of inhibiting cell growth, i.e., inhibiting cancer cell growth by inhibiting HIG2 expression. HIG2 expression can be inhibited through the use of small interfering RNA (siRNA) that specifically target of the HIG2 gene. An HIG2 target includes, for example, nucleotide sequences of SEQ ID NO:77-80.

In non-mammalian cells, double-stranded RNA (dsRNA) has been shown to exert a strong and specific silencing effect on gene expression, which is referred as RNA interference (RNAi) (Sharp P A. RNAi and double-strand RNA. Genes Dev. 1999 Jan. 15; 13(2):139-41). dsRNA can be processed into 20-23 nucleotides dsRNA called small interfering RNA (siRNA) by an enzyme containing RNase III motif. These siRNA specifically target complementary mRNA with a multicomponent nuclease complex (Hammond S M, Bernstein E, Beach D, Hannon G J. An RNA-directed nuclease mediates post-transcriptional gene silencing in *Drosophila* cells. Nature. 2000 Mar. 16; 404(6775):293-6., Hannon G J. RNA interference. Nature. 2002 Jul. 11; 418(6894):244-51). In mammalian cells, siRNA composed of 20 or 21-mer dsRNA with 19 complementary nucleotides and 3' terminal oncomplementary dimmers of thymidine or uridine, have been shown to have a gene-specific, knock-down effect without inducing global changes in gene expression (Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411 (6836):494-8). In addition, plasmids containing small nuclear RNA (snRNA) U6 or polymerase III H1-RNA promoter effectively produce such short RNA recruiting type III class of RNA polymerase III and thus can constitutively suppress its target mRNA (Miyagishi M, Taira K. U6 promoter-driven siRNAs with four uridine 3' overhangs efficiently suppress targeted gene expression in mammalian cells. Nat Biotechnol. 2002 May;20(5):497-500, Brummelkamp T R, Bernards R, Agami R. A System for Stable Expression of Short Interfering RNAs in Mammalian Cells Science. 296 (5567):550-553, Apr. 19, 2002).

Four different expression plasmids were constructed to express HIG2-siRNA (See Example 5). The plasmids were tested for their ability to inhibit cell growth. Various human renal carcinoma cells and normal (i.e., non-cancerous) kidney cells were transfected with HIG2-siRNA expression vectors and showed reduced number of surviving cells as compared to control plasmids.

Cell growth can also be inhibited by neutralizing HIG2 protein activity using HIG2 antibodies. For example, polyclonal antibodies were developed using a hydrophilic peptide corresponding to the C-terminal 14 amino acid residues of the HIG2 protein (EPTKGLPDHPSRSM (SEQ ID NO: 91)) and a full-length recombinant HIG2 protein excluding the N-terminal signal peptide motif. The purified antibody against HIG2 specifically recognized the HIG2 protein. The antibodies were tested for their ability to inhibit cell growth. Anti-HIG2 antibody added to the culture medium of two RCC cells, caki-1 and caki-2, suppressed their growth significantly.

In addition, the differentially expressed genes identified herein can be used for diagnostic purposes and to develop gene targeted therapeutic approaches for inhibiting renal cell carcinoma. For example, by measuring the expression of various genes in a sample of cells, the presence of renal cell carcinoma is determined in a cell or population of cells. Similarly, by measuring the expression of these genes in response to various agents, agents for treating renal cell carcinoma are identified.

Methods of Inhibiting Cell Growth

In the context of the present invention, the growth of cells is inhibited by contacting a cell with a composition containing an HIG2 siRNA. The cell can be further contacted with a transfection agent. Suitable transfection agents are known in the art. Alternatively, growth of cells is inhibited by contacting a cell with a composition containing an HIG2 antibody or fragment thereof.

The cell can be any cell that expresses or over-expresses HIG2. For example, the cell can be a renal cell, such as a kidney cell. Alternatively, the cell can be a tumor cell, such as a carcinoma. In a preferred embodiment, the cell is a renal cell carcinoma, such as a clear cell.

In the context of the present invention, "inhibition of cell growth" encompasses cells that proliferate at a lower rate or have decreased viability as compared to cells not exposed to the composition. Cell growth can be measured by methods known in the art such as, the MTT cell proliferation assay.

HIG2-siRNA

In the context of the present invention, the HIG2-siRNA can be directed to a single target HIG2 gene sequence. Alternatively, the siRNA can be directed to multiple target HIG2 gene sequences. For example, the composition can contain HIG2-siRNA directed to two, three, four, or five or more HIG2 target sequences. In the context of the present invention, an HIG2 target sequence is a nucleotide sequence that is identical to a portion of the HIG2 gene or complementary to a portion of a naturally occurring HIG2 gene. The target sequence can include the 5' untranslated (UT) region, the open reading frame (ORF) or the 3' untranslated region of the human HIG2 gene. Alternatively, the siRNA can be a nucleic acid sequence complementary to an upstream or downstream modulator of HIG2 gene expression. Examples of upstream and downstream modulators include, but are not limited to, transcription factors that binds the HIG2 gene promoter, kinases or phosphatases that interact with the HIG2 polypeptide, HIG2 promoters and HIG2 enhancers.

HIG2-siRNA which hybridize to target mRNA decrease or inhibit production of the HIG2 polypeptide product encoded by the HIG2 gene by associating with the normally single-stranded mRNA transcript, thereby interfering with translation and thus, expression of the protein. The siRNA is preferably less than 500, less than 200, less than 100, less than 50, or less than 25 nucleotides in length. More preferably, the siRNA is 19-25 nucleotides in length. Exemplary nucleic acid sequences for the production of HIG2-siRNA include the sequences of SEQ ID NO: 77-80. Furthermore, in order to enhance the inhibition activity of the siRNA, nucleotide "u" can be added to 3'end of the antisense strand of the target sequence. The number of "u"s to be added is at least 2, generally 2 to 10, preferably 2 to 5. The added "u" form single strand at the 3'end of the antisense strand of the siRNA.

An HIG2-siRNA can be directly introduced into the cells in a form that is capable of binding to the mRNA transcripts. Alternatively, the DNA encoding the HIG2-siRNA can be in a vector.

Vectors can be produced, for example, by cloning an HIG2 target sequence into an expression vector operatively-linked regulatory sequences flanking the HIG2 sequence in a manner that allows for expression (by transcription of the DNA molecule) of both strands (Lee, N. S., Dohjima, T., Bauer, G., Li, H., Li, M.-J., Ehsani, A., Salvaterra, P., and Rossi, J. (2002) Expression of small interfering RNAs targeted against HIV-1 rev transcripts in human cells. Nature Biotechnology 20: 500-505). An RNA molecule that is antisense to HIG2 mRNA is transcribed by a first promoter (e.g., a promoter sequence 3' of the cloned DNA) and an RNA molecule that is the sense strand for the HIG2 mRNA is transcribed by a second promoter (e.g., a promoter sequence 5' of the cloned DNA). The sense and antisense strands hybridize in vivo to generate siRNA constructs for silencing of the HIG2 gene. Alternatively, two constructs can be utilized to create the sense and anti-sense strands of a siRNA construct. Cloned HIG2 can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence selected from the group consisting of nucleotides of SEQ ID NOs: 77-80, [B] is a ribonucleotide sequence consisting of 3 to 23 nucleotides, and [A'] is a ribonucleotide sequence consisting of the complementary sequence of [A]. The region [A] hybridizes to [A'], and then a loop consisting of region [B] is formed. The loop sequence is preferably 3 to 23 nucleotide in length. The loop sequence, for example, can be selected from group consisting of following sequences (on the worldwide web at ambion.com/techlib/tb/tb_506.html):

CCC (SEQ ID NO: 92), CCACC (SEQ ID NO: 93) or CCACACC (SEQ ID NO: 94) (Jacque, J. M, Triques, K., and Stevenson, M (2002) Modulation of HIV-1 replication by RNA interference. Nature, Vol. 418: 435-438);

UUCG (SEQ ID NO: 95) (Lee, N. S., Dohjima, T., Bauer, G., Li, H., Li, M.-J., Ehsani, A., Salvaterra, P., and Rossi, J. (2002) Expression of small interfering RNAs targeted against HIV-1 rev transcripts in human cells. Nature Biotechnology 20: 500-505; Fruscoloni, P., Zamboni, M., and Tocchini-Valentini, G. P. (2003) Exonucleolytic degradation of double-stranded RNA by an activity in *Xenopus laevis* germinal vesicles. Proc. Natl. Acad. Sci. USA 100(4): 1639-1644); and UUCAAGAGA (SEQ ID NO:96) (Dykxhoorn, D. M., Novina, C. D., and Sharp, P. A. (2002) Killing the messenger: Short RNAs that silence gene expression. Nature Reviews Molecular Cell Biology 4: 457-467).

Furthermore, loop sequences consisting of 23 nucleotides can also provide active siRNA (Jacque, J. M., Triques, K., and Stevenson, M. (2002) Modulation of HIV-1 replication by RNA interference. Nature 418: 435-438).

Exemplary siRNAs having hairpin loop structure suitable for use in the context of the present invention are shown below. In the following structure, the loop sequence can be selected from group consisting of, CCC (SEQ ID NO: 92), UUCG (SEQ ID NO:95), CCACC (SEQ ID NO: 93, CCACACC (SEQ ID NO: 94), and UUCAAGAGA (SEQ ID NO: 96). Preferable loop sequence is UUCAAGAGA (SEQ ID NO: 96) ("ttcaagaga" in DNA (SEQ ID NO: 97)).

```
gcatgtgataagacctcct(SEQ ID NO: 77)-[b]
-aggaggtcttatcacatgc(SEQ ID NO: 98)
(for target sequence of SEQ ID NO:77);

cactgacctagacatgtcc(SEQ ID NO: 78)-[b]
-ggacatgtctaggtcagtg(SEQ ID NO: 99)
(for target sequence of SEQ ID NO:78);

gaacctgtctaactggatg(SEQ ID NO: 79)-[b]
-catccagttagacaggttc(SEQ ID NO: 100)
(for target sequence of SEQ ID NO:79);
and cctgtctaactggatgctc(SEQ ID NO: 80)-[b]
-gagcatccagttagacagg(SEQ ID NO: 101)
(for target sequence of SEQ ID NO:80).
```

The regulatory sequences flanking the HIG2 sequence can be identical or different, such that their expression can be modulated independently, or in a temporal or spatial manner. siRNAs can transcribed intracellularly, by cloning the HIG2 gene templates into a vector containing, e.g., a RNA pol III transcription unit from the small nuclear RNA (snRNA) U6 or the human H1-RNA promoter. For introducing the vector into the cell, transfection-enhancing agent can be used. FuGENE (Rochediagnostices), Lipofectamin 2000 (Invitrogen), Oligofectamin (Invitrogen), and Nucleofactor (Wako pure Chemical) are useful as the transfection-enhancing agent.

Oligonucleotides and oligonucleotides complementary to various portions of HIG2 mRNA were tested in vitro for their ability to decrease production of HIG2 in tumor cells according to standard methods. A reduction in HIG2 gene product in cells contacted with the candidate siRNA composition as compared to cells cultured in the absence of the candidate composition can be detected using HIG2-specific antibodies or other detection strategies. Sequences which decrease production of HIG2 in in vitro cell-based or cell-free assays can then be tested for there inhibitory effects on cell growth. Sequences which inhibit cell growth in vitro can then be tested in vivo, in rats or mice, to confirm decreased HIG2 production and decreased tumor cell growth in animals with malignant neoplasms.

HIG2 Antibodies

In the context of the present invention, the HIG2 antibody can be a polyclonal antibody. Alternatively, the HIG2 antibody can be a monoclonal antibody. The amino acid sequence "EPTKGLPDHPSRSM" (SEQ ID NO: 91) is a preferred epitope to be recognized by an HIG2 antibody of the present invention. In the context of the present invention, the HIG2 antibody can be an antibody fragment or a modified antibody, so long as it binds to HIG2. For instance, the antibody fragment can be a Fab, F(ab')$_2$, Fv, or single chain Fv (scFv), in which Fv fragments from H and L chains are ligated by an appropriate linker. More specifically, a suitable antibody fragment can be generated by treating the antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. B. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. These modification methods are conventional in the field.

Alternatively, the antibody may comprise a chimeric antibody having a variable region derived from a nonhuman antibody and a constant region derived from a human antibody, or a humanized antibody having a complementarity determining region (CDR) derived from a nonhuman antibody, a frame work region (FR) and a constant region derived from a human antibody. Such antibodies can be prepared by using known technologies.

Methods of Treating Malignant Tumors

In the context of the present invention, patients with tumors characterized as over-expressing HIG2 are treated by administering HIG2-siRNA or HIG2-antibody. siRNA or antibody therapy is used to inhibit expression or activity of HIG2 in patients suffering from or at risk of developing, for example, renal cell carcinoma Such patients are identified by standard methods of the particular tumor type. For example, renal cell carcinoma can be diagnosed by computerized tomography (CT) scanning and ultrasonography.

Treatment is deemed efficacious if it leads to clinical benefit such as, for example, a reduction in the expression of HIG2, or a decrease in size, prevalence, or metastatic potential of the tumor in the subject. When treatment is applied prophylactically, the term "efficacious" indicates that the treatment retards or prevents tumors from forming or alleviates a symptom of clinical symptom of the tumor.

Symptoms and signs of renal cell carcinoma include for example, pain, hematuria, a flank mass, weight loss, fever, hypertension, night sweats, the sudden onset of a varicocele in a male patient and paraneoplastic syndromes which account for protean symptoms such as hypertension, hypercalcemia, pyrexia, and hepatic dysfunction. Efficaciousness is determined in association with any known method for diagnosing or treating the particular tumor type.

siRNA therapy is carried out by administering an siRNA to a patient by standard vectors and/or gene delivery systems. Suitable gene delivery systems include liposomes, receptor-mediated delivery systems, or viral vectors such as herpes viruses, retroviruses, adenoviruses and adeno-associated viruses, among others. A therapeutic nucleic acid composition can be formulated in conjunction with a pharmaceutically acceptable carrier. The therapeutic composition can also include a gene delivery system as described above. Pharmaceutically acceptable carriers are biologically compatible vehicles which are suitable for administration to an animal, e.g., physiological saline. A therapeutically effective amount of a composition is an amount which is capable of producing a medically desirable result, such as reduced production of a HIG2 gene product, reduction of cell growth, e.g., proliferation, or a reduction in tumor growth in a treated animal.

Parenteral administration, such as intravenous, subcutaneous, intramuscular, and intraperitoneal delivery routes, may be used to deliver HIG2-siRNA compositions of the present invention. For treatment of hepatic tumors, direct infusion the portal vein is useful.

Appropriate dosage depends upon many factors, including the patient's size, body surface area, age, the particular nucleic acid to be administered, sex, time and route of administration, general health, and other drugs being administered concurrently. Dosage for intravenous administration of nucleic acids ranges from approximately $10^6$ to $10^{22}$ copies of the nucleic acid molecule.

The polynucleotides of the present invention are administered by standard methods, such as by injection into the interstitial space of tissues such as muscles or skin, introduction into the circulation or into body cavities or by inhalation or insufflation. Such polynucleotides are generally injected or otherwise delivered to the animal with a pharmaceutically acceptable liquid carrier, e.g., a liquid carrier, which is aqueous or partly aqueous. The polynucleotides can further be associated with a liposome (e.g., a cationic or anionic liposome). The polynucleotide of the present invention preferably includes genetic information necessary for expression by a target cell, such as a promoter.

The HIG2-specific antibodies described herein are used to inhibit the growth of a tumor cell or to kill the tumor cell. For example, an antibody recognizing the amino acid sequence "EPTKGLPDHPSRSM" (SEQ ID NO: 91) as an epitope, can be used in the methods described herein. Specifically, purified antibody preparations (e.g., a purified monoclonal antibody, an antibody fragment, or single chain antibody) can be administered to an individual diagnosed with a tumor or at risk of developing a tumor. The antibody preparations can be administered using methods known in the art of passive immunization, e.g., intravenously or intramuscularly. Furthermore, the antibodies used in the methods described herein can be formulated in conjunction with a physiologically-acceptable excipient. Such excipients, e.g., physiological saline, are known in the art.

Diagnosing Renal Cell Carcinoma

In the context of the present invention, renal cell carcinoma is diagnosed by examining the expression of one or more RCCX nucleic acid from a test population of cells, (i.e., a patient derived tissue sample). Preferably, the test cell population comprises a renal cell, e.g., a cell obtained from the renal system. Gene expression can also be measured from bone marrow, blood, feces, urine, or other bodily fluids such as sputum.

Expression of one or more renal cell carcinoma-associated genes, e.g., an RCCX 1-32 gene, is determined in the test cell and compared to the expression of the normal control level. In the context of the present invention, "normal control level" refers to the expression profile of the renal cell carcinoma-associated genes typically found in a population known not to be suffering from renal cell carcinoma. An increase of the expression level of the renal cell carcinoma-associated genes in the patient-derived tissue sample as compared to a normal control level indicates that the subject is suffering from or is at risk of developing renal cell carcinoma The alteration of one or more of the renal cell carcinoma-associated genes in the test population as compared to the normal control level indicates that the test subject suffers from or is at risk of developing renal cell carcinoma For example, an alteration of at least 10%, at least 20%, at least 50%, at least 60%, at least 80%, at least 90% or more of the renal cell carcinoma-associated genes identified herein indicates a diagnosis of renal cell carcinoma.

When an expression profiling analysis shows that the expression profile contains characteristics of a renal cell carcinoma, the subject is judged to be affected with renal cell carcinoma. The term "characteristics of renal cell carcinoma" refers to a pattern of alterations in the expression levels of a set of RCCX genes, which is characteristic of the renal cell carcinoma. Specifically, for example, it is presumed that a gene whose expression level is higher in the renal cell carcinoma than in a control; when the expression level of the gene included by the expression profile is elevated as compared with that in a control, the expression profile can be assessed as having characteristics of renal cell carcinoma. When most of the pattern of alteration in the expression levels constituting the expression profile is characteristic of renal cell carcinoma, the expression profile is assessed as having characteristics of renal cell carcinoma.

Specifically, when not all but most of the RCCX genes exhibit renal cell carcinoma-associated patterns of alterations of gene expression levels, the expression profile comprising those of the RCCX genes is deemed to have characteristics of renal cell carcinoma.

When 50% or more, preferably 60% or more, more preferably 80% or more, still preferably 90% or more of the RCCX genes constituting the expression profile exhibit renal cell carcinoma-associated patterns of alterations of gene expression levels, it is concluded that the expression profile has characteristics of renal cell carcinoma.

In the present invention, a diagnostic agent for diagnosing renal cell carcinoma is also provided. The diagnostic agent of the present invention comprises a compound or composition that binds to the DNA or protein of a RCCX gene. Preferably, an oligonucleotide that hybridizes to the polynucleotide of a RCCX gene, or an antibody that specifically binds to the protein encoded by a RCCX gene may be used as the compound or composition.

Alternatively, a protein of an RCCX gene can be detected by an immunological method. A person skilled in the art may select any immunoassay format. For example, enzyme-linked immunosorbent assay (ELISA), enzyme immunoassay (EIA), radioimmunoassay (RIA), and/or immunofluorescence may be used to detect and measure the protein. In ELISA, an antibody that recognizes the protein is immobilized on a solid phase, and a sample containing the protein is applied to the solid phase. A plate, microbeads, or magnetic beads are used as a solid phase. Then, a secondary antibody that recognizes the protein and is labeled with an enzyme, such as alkaline phosphatase, is applied, and the solid phase is incubated. Next, after washing, an enzyme substrate, such as p-nitrophenyl phosphate, is added to the solid phase, and the absorbance is measured to evaluate the antigen binding activity of the sample.

In the present invention, a protein of an RCCX gene to be determined is preferably derived from a bodily fluid collected from a subject to be diagnosed. A bodily fluid sample includes a blood sample or blood-derived sample. such as serum, plasma, or whole blood. The protein concentration in the sample taken from a subject to be diagnosed (i.e, the test sample) is preferably compared with that in control, such as a sample from a normal subject (i.e., the normal sample). When such a comparison shows that the expression level of the protein in the test sample is higher than that in the normal sample, the subject is judged to be affected with an RCC. The expression level of the protein in the normal sample and the test sample can be determined simultaneously. Alternatively, normal ranges of the expression levels can be statistically determined using the expression level of the protein in specimens previously collected from a control group. The expression level in the test sample is compared with the normal range; when the level does not fall within the normal range, the subject is judged to be affected with RCC. The expression level of HIG2 is preferably determined as the protein of an RCCX in the diagnostic method of the present invention.

Identifying Agents that Inhibit Renal Cell Carcinoma-Associated Gene Expression

An agent that inhibits the expression or activity of a renal cell carcinoma-associated gene is identified by contacting a test cell population expressing a renal cell carcinoma-associated gene with a test agent and determining the expression level of the renal cell carcinoma associated gene. A decrease in expression of a renal cell carcinoma-associated gene as compared to a control level indicates that the agent is an inhibitor of a renal cell carcinoma-associated gene and, thus, useful in inhibiting renal cell carcinoma The test cell population can be any cell expressing the renal cell carcinoma-associated genes. For example, the test cell population can contain a renal cell. More particularly, the test cell can be an immortalized cell line derived from a renal cell carcinoma cell.

Assessing the Efficacy of Treatment of Renal Cell Carcinoma in a Subject

A differentially expressed RCC-associated gene identified herein also allows for the course of treatment of renal cell carcinoma to be monitored. In this method, a test cell population is provided from a subject undergoing treatment for renal cell carcinoma. If desired, test cell populations can be obtained from the subject at various time points, before, during, and/or after treatment. Expression of one or more of the RCC-associated genes in the cell population is then determined and compared to a reference cell population, which includes cells whose renal cell carcinoma state is known. The reference cells should not have been exposed to the treatment.

If the reference cell population contains no renal cell carcinoma cells, a similarity in expression of RCC-associated genes between the test cell population and the reference cell population indicates that the treatment is efficacious or conferring clinical benefit. However, a difference in expression of RCC-associated gene between the test population and the reference cell population indicates a less favorable clinical outcome or prognosis.

The term "efficacious" indicates, for example, that the treatment leads to a reduction in expression of a pathologically up-regulated gene, or a decrease in size, prevalence, or metastatic potential of renal cell carcinoma in a subject. When treatment is applied prophylactically, the term "efficacious" means that the treatment retards or prevents renal cell carcinoma from forming. Assessment of the stage of renal cell carcinoma is made using standard clinical protocols.

Efficaciousness is determined in association with any known method for diagnosing or treating renal cell carcinoma.

Selecting a Therapeutic Agent for Treating Renal Cell Carcinoma that is Appropriate for a Particular Individual Differences in the genetic makeup of individuals can result in differences in their relative abilities to metabolize various drugs. An agent that is metabolized in a subject to act as an anti-renal cell carcinoma agent can manifest itself by inducing a change in gene expression pattern in the subject's cells, from that characteristic of a cancerous state to a gene expression pattern characteristic of a non-cancerous state. Accordingly, the differentially expressed RCC-associated genes disclosed herein allow for a putative therapeutic or prophylactic anti-renal cell carcinoma agent to be tested in a test cell population from a selected subject in order to determine if the agent is a suitable anti-renal cell carcinoma agent for the subject.

To identify an anti-renal cell carcinoma agent that is appropriate for a specific subject, a test cell population from the subject is exposed to a therapeutic agent, and the expression of one or more of the RCCX 1-32 genes determined.

The test cell population should contain a renal cell carcinoma cell expressing at least one renal cell carcinoma associated gene. Preferably, the test cell is a kidney cell. For example, a test cell population can be incubated in the presence of a candidate agent and the pattern of gene expression of the test sample can be measured and compared to one or more reference profiles, e.g., a renal cell carcinoma reference expression profile or an non-renal cell carcinoma reference expression profile.

A decrease in expression of one or more of the RCCX 1-32 genes in a test cell population relative to a reference cell population containing renal cell carcinoma indicates that the agent is therapeutic. The test agent may comprise any compound or composition. For example, the test agents can be immunomodulatory agents or specific antisense nucleotide compounds which correspond to an aberrantly over-expressed RCCX nucleic acid.

Screening Assays for Identifying Therapeutic Agents

The differentially expressed sequences disclosed herein can also be used to identify candidate therapeutic agents for treating renal cell carcinoma. The method is based on screening a candidate therapeutic agent to determine if it converts an expression profile of an RCCX 1-32 gene characteristic of a renal cell carcinoma state to a pattern indicative of or more similar to that of a clinical state that is not associated with renal cell carcinoma.

In the method of the present invention, a cell is exposed to a test agent or a combination of test agents (sequentially or consecutively) and the expression of one or more RCCX 1-32 gene in the cell is measured. The expression profile of the RCCX nucleic acid(s) in the test population is compared to expression level of the RCCX nucleic acid(s) in a reference cell population that is not exposed to the test agent.

In the screening method of the present invention, when marker genes whose expression levels are increased in renal cell carcinoma, candidate agents to be selected should have the activity of decreasing the expression levels as compared with those in a control.

Alternatively, the screening of the present invention may comprise the steps described below: (1) contacting a candidate agent with a protein encoded by a marker gene; and (2) selecting a candidate agent that alters the activity of the protein as compared with that in a control.

The protein required for the screening can be obtained as a recombinant protein by using the nucleotide sequence of the marker gene. Based on the information related to the marker gene, one skilled in the art can select the biological activity of a protein as an index of screening and a suitable method for measuring the selected activity.

Alternatively, the screening of the present invention may comprise the steps described below.

(1) preparing a reporter construct that ensures the expression of the reporter gene under control of the transcriptional regulatory region of a marker gene;

(2) contacting a candidate agent with host cells containing and capable of expressing the above-mentioned reporter construct; and (3) measuring the activity or expression level of the reporter gene, and selecting the candidate agent having an activity of altering the expression level when compared with that in a control.

The reporter construct required for the screening can be prepared by using the transcriptional regulatory region of a marker gene. When the transcriptional regulatory region of a marker gene is known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

There is no limitation on the type of candidate agent that may be used in the screening method of the present invention. The candidates of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

An agent effective in suppressing expression of one or more over-expressed genes is deemed to lead to a clinical benefit. Such compounds are further tested for the ability to prevent cancer cell growth.

Assessing the Prognosis of a Subject with Renal Cell Carcinoma

Also provided herein is a method of assessing the prognosis of a subject with renal cell carcinoma by comparing the expression of one or more RCC-associated gene in a test cell population with the expression of the same genes in a reference cell population derived from patients over a spectrum of disease stages. By comparing gene expression of one or more RCC-associated genes in the test cell population and the reference cell population(s), or by comparing the pattern of gene expression over time in test cell populations derived from the subject, the prognosis of the subject can be assessed. For example, an increase in expression of one or more of RCCX 1-32 gene over time as compared to a normal control indicates less favorable prognosis.

Kits

The present invention also includes an RCCX-detection reagent, e.g., a nucleic acid that specifically binds to or identifies one or more RCCX nucleic acid, such as oligonucleotide sequences which are complementary to a portion of an RCCX nucleic acid or antibodies which bind to proteins encoded by an RCCX nucleic acid. The reagents can be packaged together in the form of a kit. The reagents can be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay can be included in the kit. The assay format of the kit is a Northern hybridization or a sandwich ELISA known in the art.

For example, an RCCX detection reagent can be immobilized on a solid matrix such as a porous strip to form at least one RCCX detection site. The measurement or detection region of the porous strip may include a plurality of sites containing a nucleic acid. A test strip may also contain sites for negative and/or positive controls. Alternatively, control sites can be located on a strip separate from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of RCCX present in the sample. The detection sites may be configured in any suitably detectable shape and are typically in the shape of a bar or dot spanning the width of a test strip.

Alternatively, the kit can contain a nucleic acid substrate array comprising one or more nucleic acid sequences. The nucleic acids on the array specifically identify one or more nucleic acid sequences represented by the RCCX 1-32 genes. The expression of 2, 3, 4, 5, 6, 7, 8, 9, 10, 15, 20, 25, or more of the sequences represented by the RCCX 1-32 genes are identified by virtue of the level of binding to an array test strip or chip. The substrate array can be on, e.g., a solid substrate, e.g., a "chip" as described in U.S. Pat. No. 5,744,305.

Likewise, an antibody binding to a protein of an RCCX gene can be contained in the kit. Preferably, the antibody is fixed on a solid phase such as a plate, micro beads, or magnetic beads. Furthermore, the antibody fixed on the solid phase can be combined with a second antibody labeled with a label such as a signal generating molecule. Enzyme, fluorophor, or luminescence molecules are examples of suitable signal generating molecules. The kit comprising the antibody can further comprise a detection reagent for the signal generated by the label.

Arrays and Pluralities

The present invention also includes a nucleic acid substrate array comprising one or more nucleic acid sequences. The nucleic acids on the array specifically correspond to one or more nucleic acid sequences represented by the RCCX 1-32 genes. The level of expression of 2, 3, 4, 5, 6, 7, 8, 9, 10, 15, 20, 25, or more of the sequences represented by the RCCX 1-32 genes can be identified by detecting nucleic acid binding to the array.

The invention also includes an isolated plurality (i.e., a mixture of two or more nucleic acids) of nucleic acid sequences. The nucleic acid sequence can be in a liquid phase or a solid phase, e.g., immobilized on a solid support such as a nitrocellulose membrane. The plurality includes one or more of the nucleic acid sequences represented by the RCCX 1-32 genes. In various embodiments, the plurality includes 2, 3, 4, 5, 6, 7, 8, 9, 10, 15, 20, 25, or more of the sequences represented by the RCCX 1-32 genes.

The DNA array is a device that is convenient to compare expression levels of a number of genes at the same time. DNA array-based expression profiling can be carried out, for example, by the method disclosed in "Microarray Biochip Technology" (Mark Schena, Eaton Publishing, 2000), etc.

A DNA array comprises immobilized high-density probes to detect a number of genes. Thus, expression levels of many genes can be estimated at the same time by a single-round analysis. Namely, the expression profile of a specimen can be determined with a DNA array. Accordingly, a DNA array-based method of the present invention preferably comprises the following steps of:

(1) synthesizing aRNAs or cDNAs, including those of the marker genes;

(2) hybridizing the aRNAs or cDNAs with probes for marker genes; and (3) detecting the aRNA or cDNA hybridizing with the probes and quantifying the amount of mRNA thereof.

The term "aRNA" refers to RNA transcribed from a template cDNA with RNA polymerase (i.e., amplified RNA). An aRNA transcription kit for DNA array-based expression profiling is commercially available. With such a kit, aRNA can be synthesized from T7 promoter-attached cDNA as a template by using T7 RNA polymerase. On the other hand, by PCR using random primers, cDNA can be amplified using as a template a cDNA synthesized from mRNA.

Alternatively, the DNA array can comprise probes spotted thereon to detect the marker genes of the present invention. There is no limitation on the number of marker genes to be spotted on the DNA array. For example, one may select 5% or more, preferably 20% or more, more preferably 50% or more, still more preferably 70% or more of the marker genes of the present invention. Other genes in addition to the marker genes of the present invention can also be spotted on the DNA array. For example, a probe for a gene whose expression level is hardly altered may be spotted on the DNA array. Such a gene can be used to normalize assay results when assay results are intended to be compared between multiple chips or between different assays.

A probe is designed for each marker gene selected, and spotted on a DNA array. Such a probe may be, for example, an oligonucleotide comprising 5-50 nucleotide residues. A method for synthesizing such oligonucleotides on a DNA array is known to those skilled in the art. Longer DNAs can be synthesized chemically or by PCR. A method for spotting long DNA synthesized by PCR or the like onto a glass slide is also known to those skilled in the art. A DNA array that is obtained by the methods described above can be used for diagnosing renal cell carcinoma according to the present invention.

For example, the prepared DNA array is contacted with aRNA, followed by the detection of hybridization between the probe and aRNA. The aRNA can be previously labeled with a fluorescent dye. A fluorescent dye such as Cy3 (red) and Cy5 (green) can be used to label a aRNA. aRNAs from a subject and a control are labeled with different fluorescent dyes, respectively. The difference in the expression level between the two can be estimated based on a difference in the signal intensity. The signal of fluorescent dye on the DNA array can be detected by a scanner and analyzed by using a special program. For example, the Suite from Affymetrix is a software package for DNA array analysis.

Methods of Inhibiting RCC

The present invention further provides a method for treating or alleviating one or more symptoms of RCC in a subject by decreasing expression or activity of one or more of the RCCX 1-32 genes. Therapeutic compounds can be administered prophylactically or therapeutically to subject suffering from (or susceptible to) developing RCC. Administration can be systemic or local. Such subjects can be identified using standard clinical methods or by detecting an aberrant level of expression or activity of an RCCX 1-32 gene. Therapeutic agents include inhibitors of cell proliferation.

The method of the present invention includes the step of decreasing the expression, or function, or both, of gene products of the RCCX 1-32 genes. Expression may be inhibited in any of several ways known in the art. For example, expression can be inhibited by administering to the subject a nucleic acid that inhibits, or antagonizes, the expression of an over-expressed gene, e.g., an antisense oligonucleotide or small interfering RNA (siRNA) which disrupts expression of the over-expressed gene.

As noted above, antisense nucleic acids corresponding to the nucleotide sequence of an RCCX 1-32 gene can be used to reduce the expression level of an RCCX 1-32 gene. Antisense nucleic acids corresponding to the nucleotide sequence of an RCCX 1-32 gene that is up-regulated in RCC are useful for the treatment of RCC. Specifically, the antisense nucleic acids of the present invention may act by binding to the nucleotide sequence of an RCCX 1-32 gene or mRNA corresponding thereto, thereby inhibiting the transcription or translation of the gene, promoting the degradation of the mRNA, and/or inhibiting the expression of protein encoded by a nucleic acid of an RCCX 1-32 gene, finally inhibiting the function of the proteins. The term "antisense nucleic acids" as used herein encompasses both nucleotides that are entirely complementary to the target sequence and those having a mismatch of nucleotide, so long as the antisense nucleic acids can specifically hybridize to the target sequences. For example, the antisense nucleic acids of the present invention include polynucleotides that have a homology of at least 70% or higher, preferably at 80% or higher, more preferably 90% or higher, even more preferably 95% or higher over a span of at least 15 continuous nucleotides. Algorithms known in the art can be used to determine the homology.

The antisense nucleic acids of the present invention act on cells producing the protein encoded by marker gene by binding to the DNA or mRNA encoding the protein, inhibiting their transcription or translation, promoting the degradation of the mRNA, and inhibiting the expression of the protein, thereby resulting in the inhibition of the protein function.

An antisense nucleic acid of the present invention can be made into an external preparation, such as a liniment or a poultice, by mixing with a suitable base material which is inactive against the derivative.

Also, as needed, the antisense nucleic acids can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense nucleic acids of the present invention can be given to the patient by directly applying it onto the ailing site or by injecting it into a blood vessel so that it will reach the site of ailment. An antisense-mounting medium can also be used to increase durability and membrane-permeability. Examples include, but are not limited to, liposomes, poly-L-lysine, lipids, cholesterol, lipofectin or derivatives of these.

The dosage of the antisense nucleic acid of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of the protein of the present invention and thereby are useful for suppressing the biological activity of the protein. Also, expression-inhibitors, comprising antisense nucleic acids of the present invention, are useful in that they can inhibit the biological activity of a protein of the present invention.

The antisense nucleic acids of present invention include modified oligonucleotides. For example, thioated oligonucleotides may be used to confer nuclease resistance to an oligonucleotide.

Also, a siRNA against marker gene can be used to reduce the expression level of the marker gene. By the term "siRNA" is meant a double stranded RNA molecule which prevents translation of a target mRNA. Standard techniques of introducing siRNA into the cell are used, including those in which DNA is a template from which RNA is transcribed. In the context of the present invention, the siRNA comprises a sense nucleic acid sequence and an anti-sense nucleic acid sequence against an up-regulated marker gene, such as HIG2. The siRNA is constructed such that a single transcript has both the sense and complementary antisense sequences from the target gene, e.g., a hairpin.

The method is used to alter the expression in a cell of an up-regulated, e.g., as a result of malignant transformation of the cells. Binding of the siRNA to a transcript corresponding to an RCCX 1-32 gene in the target cell results in a reduction in the protein production by the cell. The length of the oligonucleotide is at least 10 nucleotides and may be as long as the naturally-occurring the transcript. Preferably, the oligonucleotide is 19-25 nucleotides in length. Most preferably, the oligonucleotide is less than 75, 50, 25 nucleotides in length. Examples of HIG2 siRNA oligonucleotide which inhibit the expression in mammalian cells include the target sequence containing SEQ ID NO: 77-80.

The nucleotide sequence of the siRNAs can be designed using a siRNA design computer program available from the Ambion website (on the worldwide web at ambion.com/techlib/misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/.
3. Select qualifying target sequences for synthesis. At Ambion, preferably several target sequences can be selected along the length of the gene for evaluation.

The antisense oligonucleotide or siRNA of the present invention inhibit the expression of the polypeptide encoded by an RCCX 1-32 gene and is thereby useful for suppressing the biological activity of the polypeptide. Also, expression-inhibitors, comprising antisense oligonucleotides or siRNA of the invention, are useful in that they can inhibit the biological activity of a polypeptide encoded by an RCCX 1-32 gene. Therefore, a composition comprising an antisense oligonucleotide or siRNA of the present invention is useful in treating RCC.

Alternatively, the function of gene product of the overexpressed gene can be inhibited by administering a compound or composition that binds to or otherwise inhibits the function of the gene product. For example, the compound or composition may comprise an antibody which binds to the over-expressed gene product.

The present invention refers to the use of antibodies, particularly antibodies against a protein encoded by an up-regulated marker gene, or a fragment of the antibody. As used herein, the term "antibody" refers to an immunoglobulin molecule having a specific structure, that interacts (i.e., binds) only with the antigen that was used for synthesizing the antibody (i.e., the up-regulated marker gene product) or with an antigen closely related to it. Furthermore, an antibody may be a fragment of an antibody or a modified antibody, so long as it binds to the protein encoded by the RCCX 1-32 gene. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field.

Alternatively, an antibody may comprise a chimeric antibody having a variable region derived from a nonhuman antibody and a constant region derived from a human antibody, or a humanized antibody having the complementarity determining region (CDR) derived from a nonhuman antibody, the frame work region (FR) and the constant region derived from a human antibody. Such antibodies can be prepared by using known technologies.

Cancer therapies directed at specific molecular alterations that occur in cancer cells have been validated through clinical development and regulatory approval of anti-cancer drugs such as trastuzumab (Herceptin) for the treatment of advanced breast cancer, imatinib methylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F, Tortora G. A novel approach in the treatment of cancer: targeting the epidermal growth factor receptor. Clin Cancer Res. 2001 October; 7(10):2958-70. Review; Slamon D J, Leyland-Jones B, Shak S, Fuchs H, Paton V, Bajamonde A, Fleming T, Eiermann W, Wolter J, Pegram M, Baselga J, Norton L. Use of chemotherapy plus a monoclonal antibody against HER2 for metastatic breast cancer that overexpresses HER2. N Engl J Med. 2001 Mar. 15; 344(11):783-92; Rehwald U, Schulz H, Reiser M, Sieber M, Staak J O, Morschhauser F, Driessen C, Rudiger T, Muller-Hermelink K, Diehl V, EngertA. Treatment of relapsed CD20+ Hodgkin lymphoma with the monoclonal antibody rituximab is effective and well tolerated: results of a phase 2 trial of the German Hodgkin Lymphoma Study Group. Blood. 2003 Jan. 15; 101 (2):420-424; Fang G, Kim C N, Perkins C L, Ramadevi N, Winton E, Wittmann S and Bhalla K N. (2000). Blood, 96, 2246-2253). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56; Klejman A, Rushen L, Morrione A, Slupianek A and Skorski T. (2002). Oncogene, 21, 5868-5876). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The method involves administering a protein or combination of proteins or a nucleic acid molecule or combination of nucleic acid molecules as therapy to counteract aberrant expression or activity of the differentially expressed genes.

Diseases and disorders that are characterized by increased (relative to a subject not suffering from the disease or disorder) expression levels or biological activity of the genes may be treated with therapeutics that antagonize (i.e., reduce or inhibit) activity of the over-expressed gene or genes. Therapeutics that antagonize activity can be administered therapeutically or prophylactically.

Therapeutics that may be utilized include, e.g., (i) a polypeptide of the over-expressed sequence, or analogs, derivatives, fragments or homologs thereof (ii) antibodies to the over-expressed sequence (iii) nucleic acids encoding the over-expressed sequence; (iv) antisense nucleic acids or nucleic acids that are "dysfunctional" (i.e., due to a heterologous insertion within the coding sequence of over-expressed sequence); (v) small interfering RNA (siRNA); or (vi) modulators (i.e., inhibitors, agonists and antagonists that alter the interaction between an over-expressed polypeptide and its binding partner). The dysfunctional antisense molecule is utilized to "knockout" endogenous function of a polypeptide by homologous recombination (see, e.g., Capecchi, Science 244: 1288-1292 1989).

Increased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods of the present invention include the step of contacting a cell with an agent that modulates one or more of the activities of the differentially expressed gene product. An agent that modulates protein activity includes a nucleic acid or a protein, a naturally-occurring cognate ligand of such a protein, a peptide, a peptidomimetic, or other small molecule.

The present invention also relates to a method of treating or preventing RCC in a subject comprising the step of administering to said subject a vaccine comprising a polypeptide encoded by an RCCX 1-32 gene or an immunologically active fragment of such a polypeptide, or a polynucleotide encoding the polypeptide or the fragment thereof. Administration of the polypeptide induces an anti-tumor immunity in a subject. To induce anti-tumor immunity, a polypeptide encoded by an RCCX 1-32 gene or an immunologically active fragment of such a polypeptide, or a polynucleotide encoding the polypeptide is administered. The polypeptide or the immunologically active fragments thereof are useful as vaccines against RCC. In some cases, the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the context of the present invention, a vaccine against RCC refers to a substance that has ability to induce anti-tumor immunity upon inoculation into animals. According to the present invention, polypeptides encoded by an RCCX 1-32 gene or fragments thereof were suggested to be HLA-A24 or HLA-A*0201 restricted epitopes peptides that may induce potent and specific immune response against RCC cells expressing an RCCX 1-32 gene. Thus, the present invention also encompasses methods of inducing anti-tumor immunity using the polypeptides. In general, anti-tumor immunity includes immune responses such as follows:
 induction of cytotoxic lymphocytes against tumors,
 induction of antibodies that recognize tumors, and
 induction of anti-tumor cytokine production.

Therefore, when a certain protein induces any one of these immune responses upon inoculation into an animal, the protein is deemed to have anti-tumor immunity inducing effect. The induction of the anti-tumor immunity by a protein can be detected by observing either in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell by an APC, and detecting the induction of CTL. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTLs using dendritic cells (DCs) as the selected APC is well known in the art. DCs are representative APCs having the strongest CTL-inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DC, peripheral blood mononuclear cells (PBMCs) may also be used as the APC. The induction of CTLs has been reported to be enhanced by culturing PBMC in the presence of GM-CSF and IL-4. Similarly, CTLs have been shown to be induced by culturing PBMCs in the presence of keyhole limpet hemocyanin (KLH) and IL-7.

The test polypeptides confirmed to possess CTL-inducing activity by these methods are polypeptides having a DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are useful as vaccines against tumors. Furthermore, CTLs that have acquired cytotoxicity due to presentation of the polypeptide antigens by APCs can be also used as vaccines against tumors. Such therapeutic methods for tumors, using anti-tumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

Anti-tumor immunity is induced by administering the vaccine of this invention, and the induction of anti-tumor immunity enables treatment and prevention of RCC. Therapy against cancer or prevention of the onset of cancer includes any of the following steps, such as inhibition of the growth of cancerous cells, involution of cancer, and suppression of occurrence of cancer. Decrease in mortality of individuals having cancer, decrease in the levels of tumor markers in the blood, alleviation of detectable symptoms accompanying cancer, and such are also included in the therapy or prevention of cancer. Such therapeutic and preventive effects are preferably statistically significant, for example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Exemplary adjuvants include, but are not limited to, cholera toxin, *salmonella* toxin, alum, and such. Furthermore, the vaccine of this invention may be combined appropriately with a pharmaceutically acceptable carrier. Examples of such carriers include sterilized water, physiological saline, phosphate buffer, culture fluid, and such. Furthermore, the vaccine may contain, as necessary, stabilizers, suspensions, preservatives, surfactants, and such. The vaccine can be administered systemically or locally. Vaccine administration can be performed by single administration, or boosted by multiple administrations.

When using an APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APCs or CTLs, the cells may be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of the polypeptide of the present invention is provided. The pharmaceutical composition may be used for raising anti-tumor immunity.

Pharmaceutical Compositions for Inhibiting RCC

Pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. Preferably, administration is intravenous. The formulations are optionally packaged in discrete dosage units.

Pharmaceutical formulations suitable for oral administration include capsules, cachets or tablets, each containing a predetermined amount of the active ingredient. Formulations also include powders, granules or solutions, suspensions or emulsions. The active ingredient is optionally administered as a bolus, electuary or paste. Tablets and capsules for oral administration may contain conventional excipients, such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), or preservatives. The tablets may optionally be formulated so as to provide slow or controlled release of the active ingredient therein. A package of tablets may contain one tablet to be taken on each of the month.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example, as sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration include suppositories with standard carriers, such as cocoa butter or polyethylene glycol. Formulations for topical administration in the mouth, for example, buccally or sublingually, include lozenges, which contain the active ingredient in a flavored base, such as sucrose and acacia or tragacanth, and pastilles comprising the active ingredient in a base such as gelatin and glycerin or sucrose and acacia For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents.

For administration by inhalation the compounds can be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators.

Other formulations include implantable devices and adhesive patches; which release a therapeutic agent.

When desired, the above described formulations, adapted to give sustained release of the active ingredient, may be employed. The pharmaceutical compositions may also contain other active ingredients, such as antimicrobial agents, immunosuppressants or preservatives.

It should be understood that in addition to the ingredients particularly mentioned above, the formulations of this invention may include other agents conventional in the art with regard to the type of formulation in question. For example, formulations suitable for oral administration may include flavoring agents.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also, the route of administration may vary depending upon the condition and its severity.

The invention will be further described in the following examples, which do not limit the scope of the invention described in the claims.

Example 1

General Methods

Clinical Samples

RCC tumor and surrounding normal kidney tissues used for cDNA microarray and immunohistochemical analyses were obtained with informed consent from 10 patients who underwent surgical resection. Clinicopathological data for each case is summarized in Table 1. All were diagnosed as being at stage I or II. The paired samples were snap-frozen in liquid nitrogen immediately after surgical resection and stored at −80° C. At least 90% of the viable cells in each specimen were identified as tumor cells; accordingly, contamination with non-cancerous cells was considered to be minimal. From among these tissues, cell populations with sufficient amount and quality of RNA were selected for the microarray analysis. Plasma samples from RCC and chronic glomerulonephritis patients (CGN) used for the ELISA analyses were also obtained with informed consent. In addition, 20 plasma samples from normal healthy volunteers were also obtained with informed consent.

TABLE 1

Pathological background of 10 RCC cases

| Case ID | Histology | pTNM | Stage | Grade | Age |
|---------|-----------|---------|-------|----------|-----|
| KR-450 | clear cell | pT2N0M0 | II | G1 > G2 | 63 |
| KR-445 | clear cell | pT1bN0M0 | I | G1 >> G2 | 82 |
| KR-444 | clear cell | pT1aN0M0 | I | G1 >> G2 | 57 |
| KR-273 | clear cell | pT1bN0M0 | I | G1 > G2 | 71 |
| KR-372 | clear cell | pT1bN0M0 | I | G2 > G1 | 61 |
| KR-443 | clear cell | pT1aN0M0 | I | G2 | 76 |
| KR-394 | clear cell | pT1bN0M0 | I | G1 > G2 | 60 |
| KR-479 | clear cell | pT2N0M0 | II | G2 > G1 | 52 |
| KR-471 | clear cell | pT1aN0M0 | I | G1 | 74 |
| KR-462 | clear cell | pT1aN0M0 | I | G1 | 53 |

Cell Lines and Tissue Specimens

Cell lines derived from four RCC (A498, 786-O, caki-1, caki-2), a cervical adenocarcinoma (HeLa), nine colon cancers (SW480, SW948, LoVo, DLD1, HT29, HCT15, HCT116, SNU-C4 and SNU-C5), a breast cancer (MCF7), four hepatocellular carcinomas (Huh7, SNU475, HepG2, and Alexander), a line of human embryonic kidney cells (HEK293) and COS7 cells were grown in monolayers in appropriate media supplemented with 10% fetal bovine serum (FBS) and 1% antibiotic/antimycotic solution and maintained at 37° C. in air containing 5% $CO_2$.

cDNA Microarrays

Extraction of total RNA using TRIzol (Invitrogen) was performed according to the manufacture's instructions. After treatment with DNase I Nippon Gene, Osaka, Japan), 10 g total RNA from each tumor and corresponding normal tissue was amplified using T7 Transcription Kit (Epicentre Technologies, Madison, Wis.), and amplified RNAs were reverse transcribed in the presence of Cy5-dCTP and Cy3-dCTP, respectively (5-µg each). The labeled probes were mixed and hybridized to microarray slides containing 23,040 cDNAs, by means of an Automatic Slide Processor (Amersham Biosciences, Buckinghamshire, U.K.). The fluorescence intensities of Cy5 and Cy3 for each spot were adjusted so that the mean Cy5/Cy3 ratio of the 52 house-keeping genes was equal to one. Since data derived from low signal intensities are less reliable, a cut off value was determined for each slide and excluded genes from further analysis when both Cy3 and Cy5 provided signal intensities lower than the cut-off.

Identification of Up-Regulated Genes in RCC

The relative expression of each gene (Cy5/Cy3 intensity ratio) was defined as follows: (i) up-regulated (expression ratio >2.0), (ii) down-regulated (expression ratio <0.5), (iii) unchanged (expression ratio between 0.5 and 2.0), or (iv) not expressed (or slight expression but under the cut-off level for detection). These categories were used to detect a set of genes for which changes in the expression ratios were common among samples as well as specific to a certain subgroup in accordance with the protocol of Schena et al. To detect genes that were commonly up-regulated in RCC, the overall expression patterns of 23,040 genes on the microarray were first screened to select genes with expression ratios >2.0 that were present in >50% of the RCC cases categorized as (i), (ii), or (iii). Finally, to obtain diagnostic markers highly specific to RCC and identify potential molecular targets, the genes which did not express in normal kidney by reference to an expression database of normal human tissues were selected.

Semi-Quantitative RT-PCR Analysis

Extracted RNAs were reverse transcribed using oligo (dT)$_{21}$ primer and SuperScript II reverse transcriptase (Invitrogen). Semi-quantitative RT-PCR experiments were carried out with the same gene-specific primers as those prepared for constructing the cDNA microarray or with a tubulin alphaIII (TUBA3)-specific primer as an internal control. The primer sequences are listed in table 2. PCR reactions were optimized for the number of cycles to ensure product intensity within the logarithmic phase of amplification.

TABLE 2

Primer set for RT-PCR confirmation

| Assignment | Accession | Symbol | Forward primer sequence | SEQ ID No | Reverse primer sequence | SEQ ID No |
|---|---|---|---|---|---|---|
| 1 | AI088196 | | TGGAGCCTAAAATGGGGAAT | 3 | AGGTGCGUGAACCCATATT | 4 |
| 2 | AA010816 | | TGCCCTTTCACACACACTTT | 5 | GGAGTTGGGGGAGAAGGAGT | 6 |
| 3 | U62317 | 384D8-2 | TGTCCAGGAGACAGAGCTGA | 7 | GAGCAGTCTCAGGGACATGG | 8 |
| 4 | AA844401 | | TGCTTTCTGCATTTGGTGTT | 9 | GAATTTTGGGGTGTTTCCAA | 10 |
| 5 | AA156269 | | CAGCTGGAGACTGGCTCTCT | 11 | CAGTTTCAACAGGTAAGGCGATA | 12 |
| 6 | AI245600 | | CCAGCATTTATGGCAAATGG | 13 | TGACCCTCCAAATGTACCAAA | 14 |
| 7 | AA844729 | | CTTCTGCGTGACAACTGAGG | 15 | CTCCCAAGCATAAAACAGCA | 16 |
| 8 | AA436623 | | GCGACAAGTCAGACCTAGCC | 17 | TCTAACTGCCTCCCAGGACA | 18 |
| 9 | AA903456 | | GAGGACCTTGACTGGGTTCA | 19 | CAGGTCAAGAGACCCTTTCTTC | 20 |
| 10 | W45464 | FLJ23399 | GGGACATGGGGAGCTTAGAT | 21 | CAAAAAGGTGCACCAAAACA | 22 |
| 11 | AA251072 | | GAGCACATCCTACGCACAAG | 23 | GCTAAATTTGGGGCAATTTGT | 24 |
| 12 | AA551154 | | TGGCAAAATTCTGATGCAAA | 25 | TTGGGCTTTTTGGAAAATTG | 26 |
| 13 | AI218114 | | AGTTTGGCAGGCATGAAGAG | 27 | CGGGATCTGCACACATCTTT | 28 |
| 14 | W63748 | | CCCAAAATGGGTGTATCTGG | 29 | GGTTCTGAGCAACCTCTATAACTG | 30 |
| 15 | AA845903 | | AAGCCCAACTTTGATATAGCCTG | 31 | CTTTATTGGTGTGTTTGAGCTGG | 32 |
| 16 | AA081184 | TCF4 | TAGTCTGCTGGCTGACTGGA | 33 | ACAAGAATGAAAAAGGCCACA | 34 |
| 17 | AA171694 | CP | TCAATCCCAGAAGGAAGCTG | 35 | AAGCTATGGCCGTGAAAATG | 36 |
| 18 | AA993406 | EVA1 | CATATCTGTCTCATTCTGCCTTTT | 37 | AACAGGCCCATATTACCCCT | 38 |

TABLE 2-continued

Primer set for RT-PCR confirmation

| Assign-ment | Accession | Symbol | Forward primer sequence | SEQ ID No | Reverse primer sequence | SEQ ID No |
|---|---|---|---|---|---|---|
| 19 | U67784 | RDC1 | AGCGTGACTTTCAGTTTTGACT | 39 | AATGCAACTGTTCGTTGTGTG | 40 |
| 20 | AI273576 | NEK6 | TCCAATTGTCTGAGCTGTCG | 41 | AACTCCCAGTCACCCTGTTTT | 42 |
| 21 | L09235 | ATP6A1 | TTTCAGATCGGTCACTGATAGTATG | 43 | GTGAAATCTCAAGGATAAGGAGG | 44 |
| 22 | AA233853 | E1B-AP5 | TCGTCAACCAGCAGAGCTT | 45 | CCGCGTAGTTCATCTGCC | 46 |
| 23 | AI301935 | CFFM4 | TGTCTCCTGACCAGTGTCAGTT | 47 | TCACACTTGACCATGAGTGTTG | 48 |
| 24 | AF055460 | STC2 | ACCCTCAGCCAAGATTGGTA | 49 | TGCCTTTATTTGTCCCCTTG | 50 |
| 25 | AA872040 | INHBB | TGAACGCACATGACATAGCA | 51 | TTTTCAAATGGCAGTTTCTGA | 52 |
| 26 | T91708 | MD | CCTCCAAGCTCCTCTGACTG | 53 | TGAAAAGCAGGTGAGTCTGGT | 54 |
| 27 | AA608952 | SAGE | ACCATCAAGGAAGCAGCAAG | 55 | AACAGCTCCCTTTTTCGTAGC | 56 |
| 28 | W74530 | PYCS | GTAGGGTCTGCCTGTTGGAA | 57 | ACTAAATGCCAAGGGGACT | 58 |
| 29 | AA568223 | TOP2A | CTCTTGACCTGTCCCCTCTG | 59 | CGTTGATAACATTACTCAAGTCACA | 60 |
| 30 | AA054583 | HIG2 | AGATAGGTTGATCTCGCCCTTAC | 61 | ACACCTCTTCAACTGCTATCCAA | 62 |
| 31 | X89426 | ESM1 | GATGGATTGCAGAGAGACCTG | 63 | TCATACACACACAAACCACCAGT | 64 |
| 32 | AA165698 | | CGATACAGATATGTTCGGTGATG | 65 | CCTCCATTCTTCATCTCTCAATG | 66 |
| | AF141347 | TUBA3 | CTTGGGTCTGTAACAAAGCATTC | 67 | AAGGATTATGAGGAGGTTGGTGT | 68 |

Multi-Tissue Northern Blot Analysis

A human HIG2 (hHIG2) cDNA probe was labeled with [α-$^{32}$P] dCTP, and hybridized with Human MTN Blots (Clontech) following the supplier's manual. Pre-hybridization, hybridization and washing were performed according to the supplier's recommendations. The blots were autoradiographed with intensifying screens at −80° C. for 14 days.

Cloning and Establishment of Stable Transformants of hHIG2

The entire coding sequence of HIG2, was amplified by RT-PCR using KOD-plus DNA polymerase (TOYOBO), and inserted into the BamHI and XhoI restriction enzyme sites of pcDNA3.1(+)-Myc/His vector (Invitrogen) containing a neo-resistant gene (pcDNA3.1(+)-hHIG2-Myc/His). Constructs were confirmed by sequencing. Primer sequences were forward; 5'-TTTCTCTGCAGAGGAGTAGGG-3' (SEQ ID NO; 69) and reverse 5'-CATGCTTCTGGATGGATGG-3' (SEQ ID NO; 70). To obtain hHIG2 stable transformants, COS7 cells were transfected with pcDNA-hHIG2 using FuGene 6 (Roche diagnostics) according to the instruction manuals. Transfected cells were cultured in DMEM containing 10% FCS and GENETICIN (0.5 mg/ml). After about three weeks, 20 individual colonies were selected, and screened for stable transfectants by Limiting Dilution Assay (LDA). Each clone was checked for expression of HIG2 by RT-PCR and immunohistochemical staining methods.

Production of Recombinant hHIG2 (rhHIG2)

An HIG2 fragment encoding a hydrophobic domain (27-63 amino acid residues) was subcloned into the pET28a E. coli vector (Novagen). pET28a-hHIG2 was transformed into BL21 codon plus (Invitrogen) competent cell, and induced with 0.5 mM IPTG at 37° C. for 3 hours. rhHIG2 was purified from cleared cell lysates by TALON Metal Affinity Resins (Clontech) according to the supplier's instruction manual. Final purification of rhHIG2 was carried out on a MonoQ anion-exchanged column using ÄKTAexplorer 10S (Amersham Biosciences), and a single peak without contamination of E. coli proteins was obtained.

Polyclonal Antibody rhHIG2 protein was prepared for injection by emulsifying the antigen solution with an adjuvant. Polyclonal anti-HIG2 antibody (anti-HIG2 pAb) was raised in rabbits (Medical & Biological Laboratories, Nagoya, Japan) against the purified rhHIG2 protein. Affinity purification of the antisera was carried out as follows. rhHIG2 protein was dialyzed with 20 mM HEPES buffer (pH 8.5), and then incubated for 2 hours at with equilibrated Affi-Gel 15 gel (Bio-Rad). To block active esters of gel resin, 1M ethanolamine-HCl (pH 8.0) was added and rotated for an hour. The affinity resin-coupled ligand was transferred into a column, and equilibrated with TBS-T. The filtrated antiserum was added to the above column, and incubated at 4° C. and rotated for 2 hours. After washing with TBS-T and 50 mM Tris-HCl (pH 7.5), 1M NaCl, 1% Triton X-100, purified antibodies were eluted by 0.1M glycine-HCl (pH 2.5) supplemented 10% ethylene glycol, and then dialyzed with PBS.

Immunohistochemical Analysis

COS7 cells were transfected with 1 μg of pcDNA3.1(+)-HIG2-Myc/His plasmid mixed with FuGene6 transfection reagent (Roche, Basel, Switzerland). COS7-derived stable transfectants were washed twice with PBS(−), fixed with 4% paraformaldehyde solution for 10 min at room temperature, and rendered permeable with PBS(−) containing 0.1% Triton X-100 for 2.5 min. Cells were covered with 3% BSA in PBS(−) for 60 min to block non-specific antibody binding sites prior to reaction with the primary antibody. Myc-tagged HIG2 protein was detected with anit-HIG2 pAb as primary antibody and goat IgG fraction to rabbit IgG FITC-conjugated (ICN Biomedicals, Inc. Aurora, Ohio) as secondary antibody. Paraffin-embedded specimens of normal human tissues (heart, liver, lung, adult kidney, fetal kidney, prostate, pancreas, spinal cord; BIOCHAIN) were treated with xylene and ethanol to remove the paraffin. ENVISION+Kit/HRP (DAKO) was used to detect HIG2, after the endogenous peroxidase and protein-blocking reactions, affinity-purified rabbit anti-hHIG2 polyclonal antibody was added as primary antibody, and the mixture was treated with HRP-labeled anti-rabbit IgG as secondary antibody. Finally, substrate-chromogen was added and the tissue specimens were counterstained with hematoxylin. Experiments to inhibit immunostaining were also performed, as described previously (Mintz P J., Kim J., Do K A., Wang X., Zinner R G., Cristofanilli M., Arap M A., Hong W K., Troncoso P., Logothetis C J., Pasqualini R., Arap W. Fingerprinting the circulating repertoire of antibodies from cancer patients. *Nat Biotechnol.* 21, 57-63 (2003)).

Western Blotting

Transfected COS7 cells were maintained in serum-free medium and harvested 24 hrs and 48 hrs after transfection. Lysates and condensed culture media were separated on 15% SDS-polyacrylamide gels and transferred to a nitrocellulose membrane that was incubated with anti-HIG2 pAb. After incubation with mouse anti-human c-Myc monoclonal antibody 9E10 (Roche) and sheep anti-mouse IgG-HRP antibody (Amersham Biosciences), signals were visualized with an ECL kit (Amersham Bioscience). RCC cell lines, A498, 786-0, caki-1 and caki-2 were cultured under 5% $O_2$ for 24 hours. Endogenous HIG2 protein was detected by affinity-purified HIG2-pAb as primary antibody and sheep anti-rabbit IgG-HRP as secondary antibody (Amersham Biosciences). β-actin served as a loading control for proteins with 1:2000 dilution (clone AC-15, Sigma).

Cell Growth Assay

HIG2 stable transfectants of COS7 cells were seeded onto 6-well microtiter plate ($1 \times 10^4$ cells/well), and maintained in media containing 10% FCS supplemented 0.5 mg/ml of GENETICIN for 24 hrs, 48 hrs, 72 hrs, 96 hrs, 120 hrs, and 144 hrs. At each time point, cell proliferation was evaluated using the Cell Counting Kit (WAKO). The transfectants ($5 \times 10^3$ cells/well) were cultured in DMEM containing 0.1% FCS and 100 nM or 1 mM of BSA for 5 days after addition of recombinant hHIG2 protein, at which time cell numbers were determined again. RCC cell lines, caki-1 and caki-2 were seeded onto 12-well microplate ($1 \times 10^3$ cells/well) and cultured in McCoys'5A medium containing 0.5% FCS supplemented with 1 mM affinity-purified anti-HIG2 pAb for 5 days.

Autocrine Assay

HIG2-transfected COS7 cells were maintained in FBS-free DMEM for two days to confirm autocrine production of HIG2 during cell growth. COS7 cells were cultured in the conditioned medium of HIG2-expressed COS7 cells and non-expressed cells. The autocrine effect was neutralized by exposure to anti-HIG2 pAb at a concentration of 1 mM. Alterations in growth were monitored with a hemocytometer.

Giemsa Staining

Cells cultured on 100 mm dishes were washed twice with ice-cooled PBS(−), fixed with 4% paraformaldehyde at 4° C. for 30 min, again washed twice with PBS(−), and stained with 4% Giemsa solution.

FACS analysis. Caki-1 cells were treated with 0.5 and 1.0 μM anti-HIG2 pAb and 0.5 and 1.0 μM pre-immune rabbit IgG for 5 days, respectively. For FACS analysis, adherent and detached cells were combined and fixed with 70% ethanol at 4° C. After two rinses with PBS, cells were incubated for 30 min with 1 ml of PBS containing 1 μg of boiled RNase I at 37° C. Cells were then stained in 1 ml of PBS containing 50 μg of propidium iodide (PI). The percentages of sub-G1 fraction were determined from at least 2000 cells in a flow cytometer (FACScalibur; Becton Dickinson, San Diego, Calif.).

ELISA for HIG2. To detect and quantify HIG2 protein in the plasma of RCC patients, enzyme-linked immunosorbent assay (ELISA) was performed using affinity-purified anti-HIG2 pAb at a concentration of 10 μg/ml in 50 mM sodium carbonate to coat polystyrene plates (Nalge Nunc). Excess binding sites were blocked with 2% bovine serum albumin/PBS at 37° C. for 2 hours. Plasma from RCC patients, chronic glomerulonephritis (CGN) patients and healthy normal volunteers were incubated at 37° C. for 2 hrs. Human HIG2 protein in plasma was detected by incubating biotinylated anti-HIG2 pAb and peroxidase (HRP)-labeled avidin (DAKO) with o-phenylenediamine (DAKO) solution.

Example 2

Identification of Genes with a Clinically Relevant Expression Pattern in Renal Cell Carcinoma Cells To clarify mechanisms underlying carcinogenesis of renal cell carcinoma, genes that were commonly up-regulated in this type of tumor were searched. A cDNA microarray analysis of more than 20,000 genes in 10 tumors identified 32 genes that were up-regulated in more than 50% of the cases examined (Table 3). Up-regulation of these 32 genes was reconfirmed by semi-quantitative RT-PCR analysis (FIG. 1).

TABLE 3

32 up-regulated genes in RCC

| RCCX Assignment | Accession | Symbol | Gene Name |
|---|---|---|---|
| 1 | AI088196 | | ESTs |
| 2 | AA010816 | NM_031310 | ESTs, Weakly similar to S57447 HPBRII-7 protein [*H. sapiens*] |
| 3 | U62317 | NM_152299 384D8-2 | hypothetical protein 384D8_6 |
| 4 | AA844401 | NM_138786 | ESTs, Weakly similar to T4S1_HUMAN TRANSMEMBRANE 4 SUPERFAMILY, MEMBER 1 [*H. sapiens*] |

TABLE 3-continued 32 up-regulated genes in RCC

| RCCX Assignment | Accession | Symbol | Gene Name |
|---|---|---|---|
| 5 | AA156269 | NM_207310 | *Homo sapiens* mRNA; cDNA DKFZp434E2321 (from clone DKFZp434E2321); partial cds |
| 6 | AI245600 | | ESTs |
| 7 | AA844729 | | ESTs |
| 8 | AA436623 | | ESTs |
| 9 | AA903456 | NM_025085 | *Homo sapiens* cDNA FLJ13325 fis, clone OVARC1001762, weakly similar to N-TERMINAL ACETYLTRANSFERASE 1 (EC 2.3.1.88) |
| 10 | W45464 | NM_022763 | FLJ23399 hypothetical protein FLJ23399 |
| 11 | AA251072 | | ESTs |
| 12 | AA551154 | | ESTs |
| 13 | AI218114 | AB097022 | ESTs, Weakly similar to cytochrome P-450 [*H. sapiens*] |
| 14 | W63748 | NM_024689 | *Homo sapiens* cDNA FLJ14103 fis, clone MAMMA1001073 |
| 15 | AA845903 | NM_024898 | *Homo sapiens* cDNA: FLJ22757 fis, clone KAIA0803 |
| 16 | AA081184 | | TCF4 transcription factor 4 |
| 17 | AA171694 | NM_000096 CP | ceruloplasmin (ferroxidase) |
| 18 | AA993406 | NM_005797 EVA1 | epithelial V-like antigen 1 |
| 19 | U67784 | NM_020311 RDC1 | G protein-coupled receptor |
| 20 | AI273576 | NM_014397 NEK6 | NIMA (never in mitosis gene a)-related kinase 6 |
| 21 | L09235 | NM_001690 ATP6A1 | ATPase, H+ transporting, lysosomal (vacuolar proton pump), alpha polypeptide, 70 kD, isoform 1 |
| 22 | AA233853 | NM_002886 E1B-AP5 | E1B-55 kDa-associated protein 5 |
| 23 | AI301935 | NM_206940 CFFM4 | high affinity immunoglobulin epsilon receptor beta subunit |
| 24 | AF055460 | NM_003714 STC2 | stanniocalcin 2 |
| 25 | AA872040 | NM_002193 INHBB | inhibin, beta B (activin AB beta polypeptide) |
| 26 | T91708 | NM_004271 MD | MD, RP105-associated |
| 27 | AA608952 | NM_018666 SAGE | putative tumor antigen |
| 28 | W74530 | NM_002860 PYCS | pyrroline-5-carboxylate synthetase (glutamate gamma-semialdehyde synthetase) |
| 29 | AA568223 | NM_001067 TOP2A | topoisomerase (DNA) II alpha (170 kD) |
| 30 | AA054583 | NM_013332 HIG2 | hypoxia-inducible protein 2 |
| 31 | X89426 | NM_007036 ESM1 | *H. sapiens* mRNA for ESM-1 protein |
| 32 | AA165698 | NM_024572 | *Homo sapiens* cDNA FLJ12691 fis, clone NT2RM4002571, weakly similar to *H. sapiens* mRNA for UDP-GalNAc: polypeptide N-acetylgalactosaminyltransferase |

Example 3

Characterization of HIG2

Figures 1, 2:
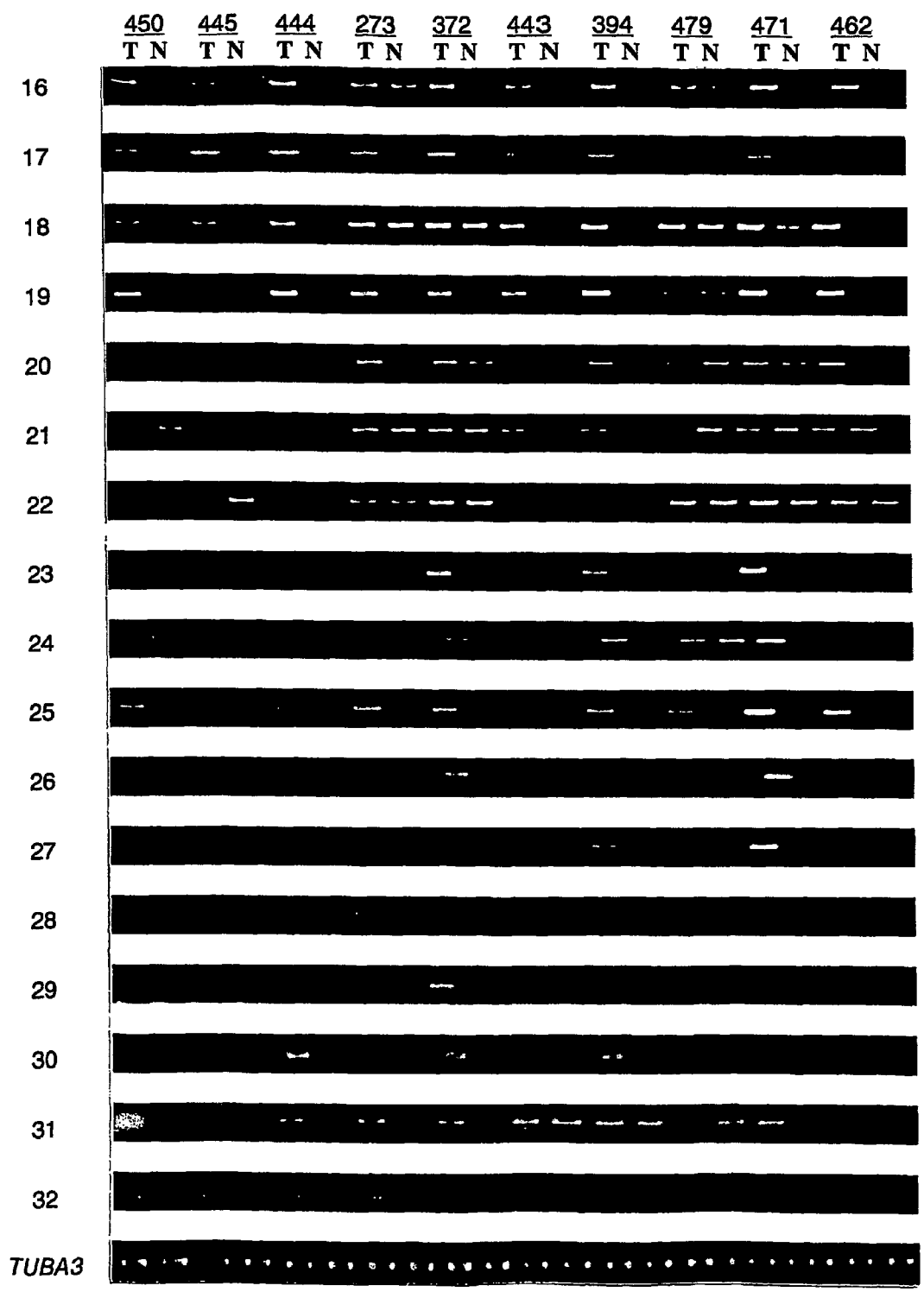
Figure 2:
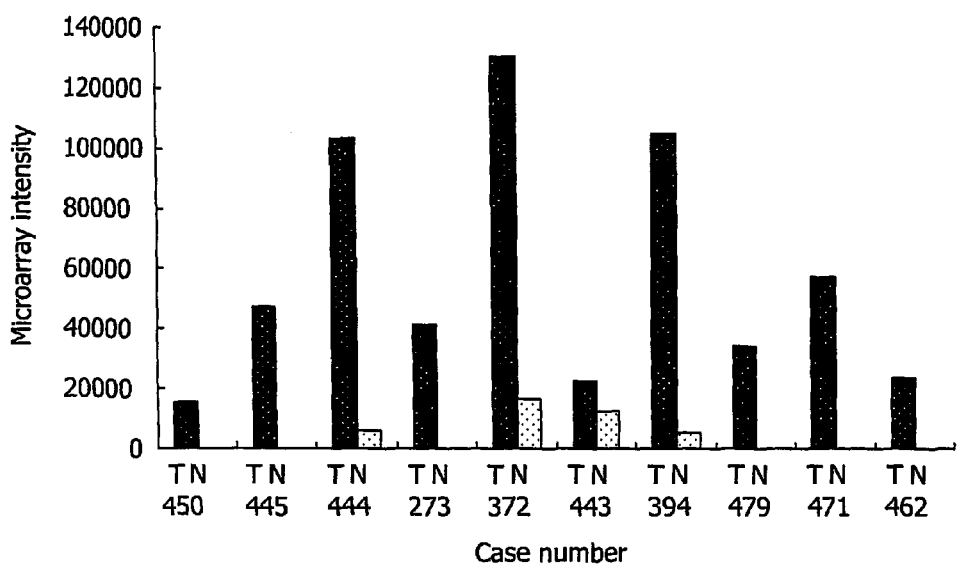
FIG. 2A is a bar chart depicting the expression profile of HIG2 in clinical RCC samples by a cDNA microarray. HIG2 transcriptional level was clearly increased in 9 of 10 RCC cases. "T" indicates tumor; "N" indicates the corresponding normal tissue
FIG. 2B is a photograph of a Northern blot showing expression levels of HIG2 in multiple tissues.
FIG. 2C is a photograph of a blot showing expression level of HIG2 measured by semi-quantitative RT-PCR in various cell lines derived from the following tumor tissues: colorectal cancer cell lines (CC), a breast cancer cell line (BC), hepatocellular carcinoma cell lines (HCC), and renal cell carcinoma cell lines (RCC).
Figure 2:
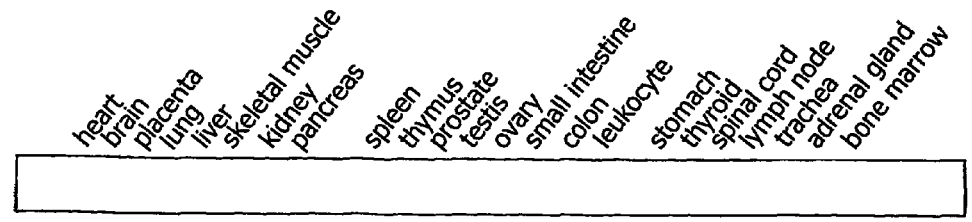
Figure 2:
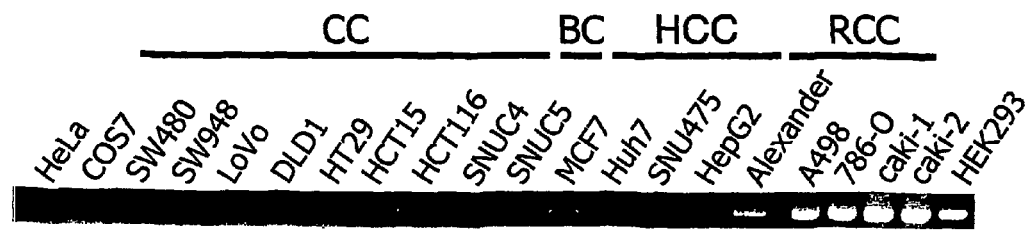

HIG2 was up-regulated in 9 of 10 RCCs examined (FIG. 1, 2a). In contrast, HIG2 expression was hardly detectable in any of the other 29 organs examined, with the exception of fetal kidney (Saito-Hisaminato A., Katagiri T., Kakiuchi S., Nakamura T., Tsunoda T., Nakamura Y. Genome-wide profiling of gene expression in 29 normal human tissues with a cDNA microarray. *DNA Res.* 9, 35-45 (2002)). Multi-tissue northern (MTN) blot analysis also demonstrated that HIG2 expression was uniformly low level, confined to trachea, spinal cord and thyroid (FIG. 2b).

To further examine the expression level of HIG2 in tumors other than renal cell carcinomas, RT-PCR analysis was performed using cancer cell lines derived from various tissues. HIG2 was expressed strongly in RCC cell lines, but at very low levels in cancer cell lines derived from other organs, including colon cancer (CC), breast cancer (BC), and hepatocellular carcinoma (HCC) cell lines (FIG. 2c).

Figures 2, 3:
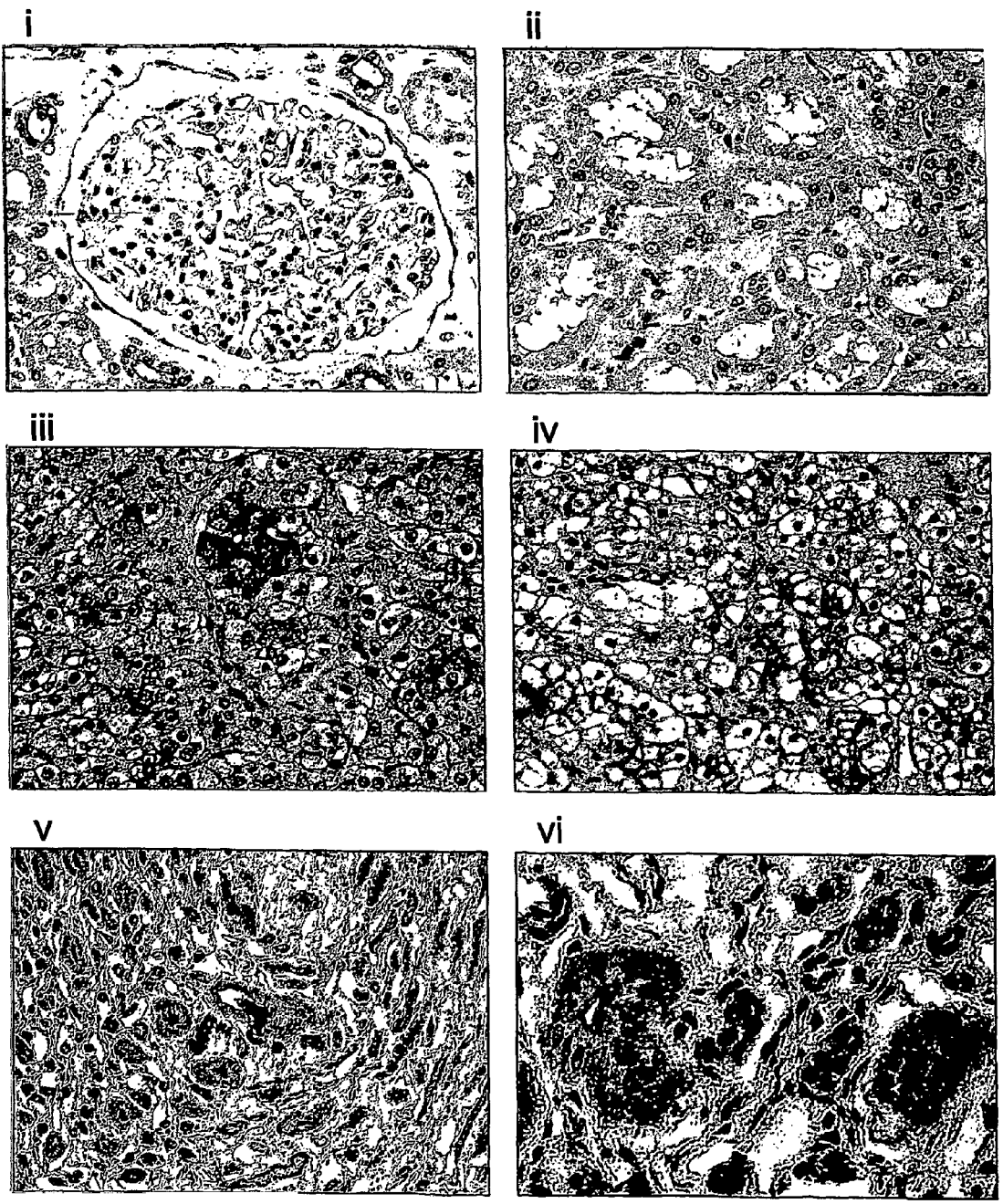
FIG. 3A is a photograph of an immunoblot illustrating the specificity of purified anti-HIG2 pAb and the detection of endogenous HIG2 expression in RCC cell lines. The "mock" lane contains lysates of COS7 cells transfected with pcDNA3.1(+); the HIG2 lane contains lysate of pcDNA3.1 (+)/HIG2-transfected cells. RCC cell lines were maintained under low oxygen conditions (5% $O_2$, 95% $N_2$) to detect HIG2 clearly.
FIG. 3B is a photograph illustrating the subcellular localization of the HIG2 protein by immunofluorescent staining of myc tagged-HIG2 expressed transiently in COS7. HIG2 was detected using mouse anti-myc antibody and FITC-conjugated anti-mouse IgG.
FIG. 3C is a photograph of a immunoblot illustrating the confirmation of HIG2 as a secretory protein using cell lysate (CL) and culture media (CM). Detection of HIG2 was performed using an anti-HIG2 antibody.
FIG. 3D are photographs of immunohistochemical staining of HIG2 protein in the following tissues: human adult kidney (i, ii), renal cell carcinoma (iii, iv), and fetal kidney (v, vi) sections with anti-HIG2 antibody. Strong expression was detected in RCC and fetal kidney, and no staining was detected in normal kidney.
FIG. 3E are photographs of immunohistochemical staining of HIG2 protein in human normal tissue sections with anti-HIG2 antibody. No expression of HIG2 protein was observed in any kind of normal human tissues.
FIG. 3F are photographs of immunohistochemical staining of HIG2 protein in normal kidney (i, ii) and RCC (iii, iv); (i, iii), before inhibition, (ii, iv), after inhibition. Addition of recombinant hHIG2 protein inhibited the staining as shown with arrow, whereas non-specific staining of polyclonal anti-HIG2 antibody was not almost detected.
FIG. 3G are photographs of immunohistochemical staining of HIG2 protein in granular and papillary type of renal cell carcinomas.
FIG. 3H are photographs of immunohistochemical staining of RCC sections with anti-HIF1αmab (i, ii) or anti-HIG2pAb (iii, iv). CN refers to the central necrotic area and arrows indicate expression of HIF1α.
Figure 3:
Figure 3:
Figure 3:
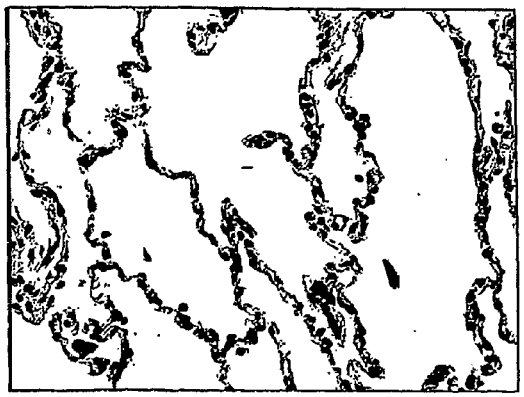
Figure 3:
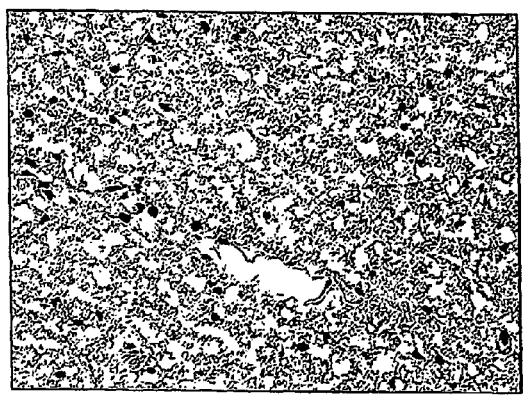
Figure 3:
Figure 3:

To confirm endogenous expression of the HIG2 product, a polyclonal antibody against HIG2 was developed. Rabbits were immunized using each of the following peptides; a hydrophilic EPTKGLPDHPSRSM (SEQ ID NO: 91) peptide corresponding to the C-terminal 14 amino acid residues and full-length recombinant HIG2 protein excluding N-terminal signal peptide motif. An antibody generated in these rabbits was purified using rhHIG2, as described in Materials and Methods. It was initially confirmed that these purified HIG2-specific polyclonal antibodies (anti-HIG2 pAb) could recognize endogenous HIG2 protein without any non-specific band in RCC cell lines (A498, 786-O, caki-1 and caki-2) (FIG. 3a). These results are consistent with those of the RT-PCR assays shown in FIG. 2c. To further investigate the extracellular secretion of the HIG2 protein, immunohistochemical staining was performed using myc-tagged HIG2 and anti-HIG2 pAb. The product of myc-tagged HIG2 revealed cytoplasmic granules distribution in secretion vesicles (FIG. 3b), as expected (Denko N., Schindler C., Koong A., Laderoute K., Green C., Giaccia A. Epigenetic regulation of gene expression in cervical cancer cells by the tumor microenvironment. *Clin Cancer Res.* 6, 480-487 (2000)). Furthermore, western blot analysis was carried out using cell lysates and culture medium of COS7 cells that had been transiently transfected with a plasmid designed to express myc-tagged HIG2 by anti-HIG2 pAb (see Materials and Methods). The HIG2 protein was detected in the culture medium and the amount of secreted protein increased in a time-dependent manner (FIG. 3c).

Immunohistochemical analyses of RCCs, as well as various organs such as heart, liver, lung, kidney, fetal kidney, spinal cord, prostate and pancreas, showed strong staining of HIG2 exclusively in RCCs (FIG. 3d; iii, iv) and fetal kidney (FIG. 3d; v, vi). Very low or no staining was observed in the remaining tissues (FIG. 3e). Inhibition of the immunohistochemical signals was also demonstrated by recombinant HIG2 protein (FIG. 3f, arrows), suggesting that anti-HIG2 pAb has the high specificity. Although the over-expression of HIG2 was identified using clear-cell type of RCC, the immunohistochemical analysis also identified expression in papillary-cell carcinomas but not in the granular type of RCCs (FIG. 3g). Abundant HIG2 expression was observed throughout RCC tissue-sections regardless to their hypoxic conditions using the anti-HIF1α mAb or anti-HIG2 pAb (FIG. 3h).

Example 4

HIG2 Modulates Cancer Cell Growth

Figures 3, 4:
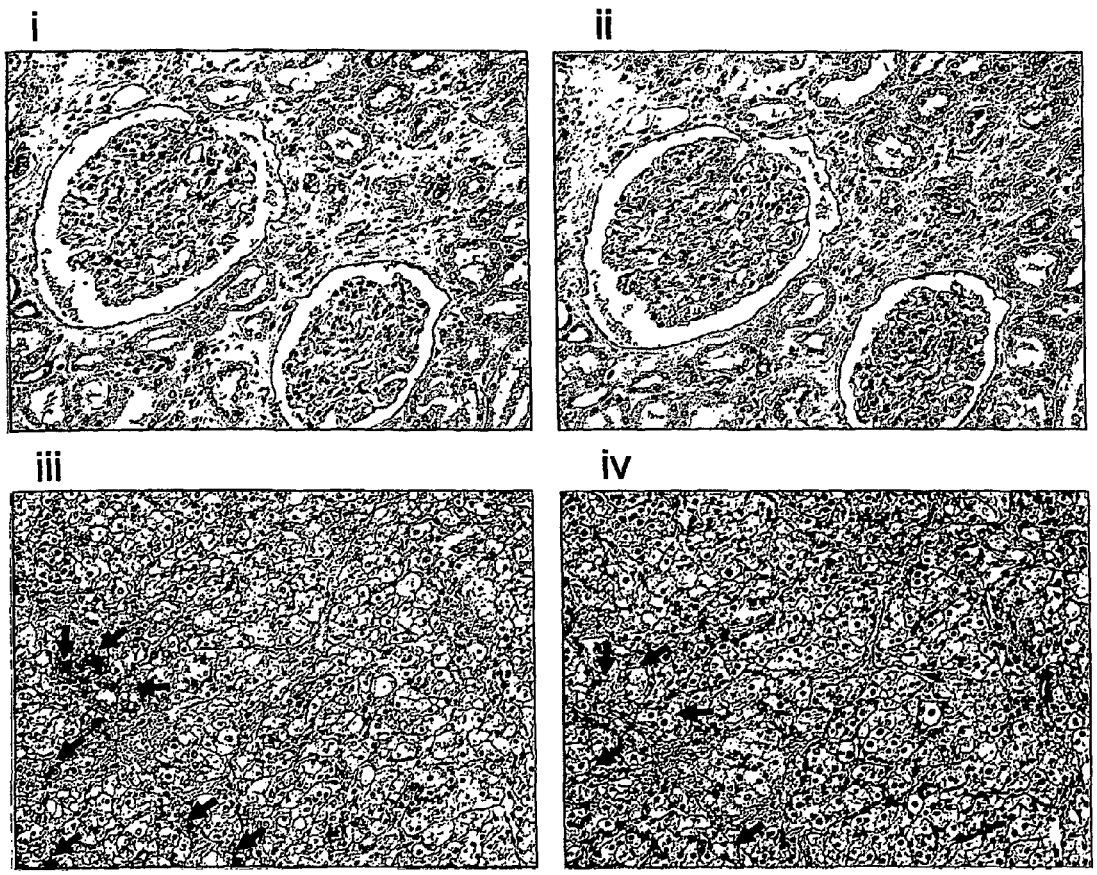
FIG. 4A is a photograph of a blot illustrating expression of HIG2 stable transformants by RT-PCR using primer sets in which the PCR product covers the HIG2 ORF.
FIG. 4B are photographs illustrating the monoclonality of established HIG2 stable transformants.
FIG. 4C is a bar chart showing the proliferation activity of HIG2 stable transformants. HIG2-stable transformants showed an increased growth rate as compared to mock-stable transformants. Bars represent the average value from three experiments±SD; *, significant difference from mock ($p<0.01$) calculated by student's t-test.
Figures 3, 4, 5:
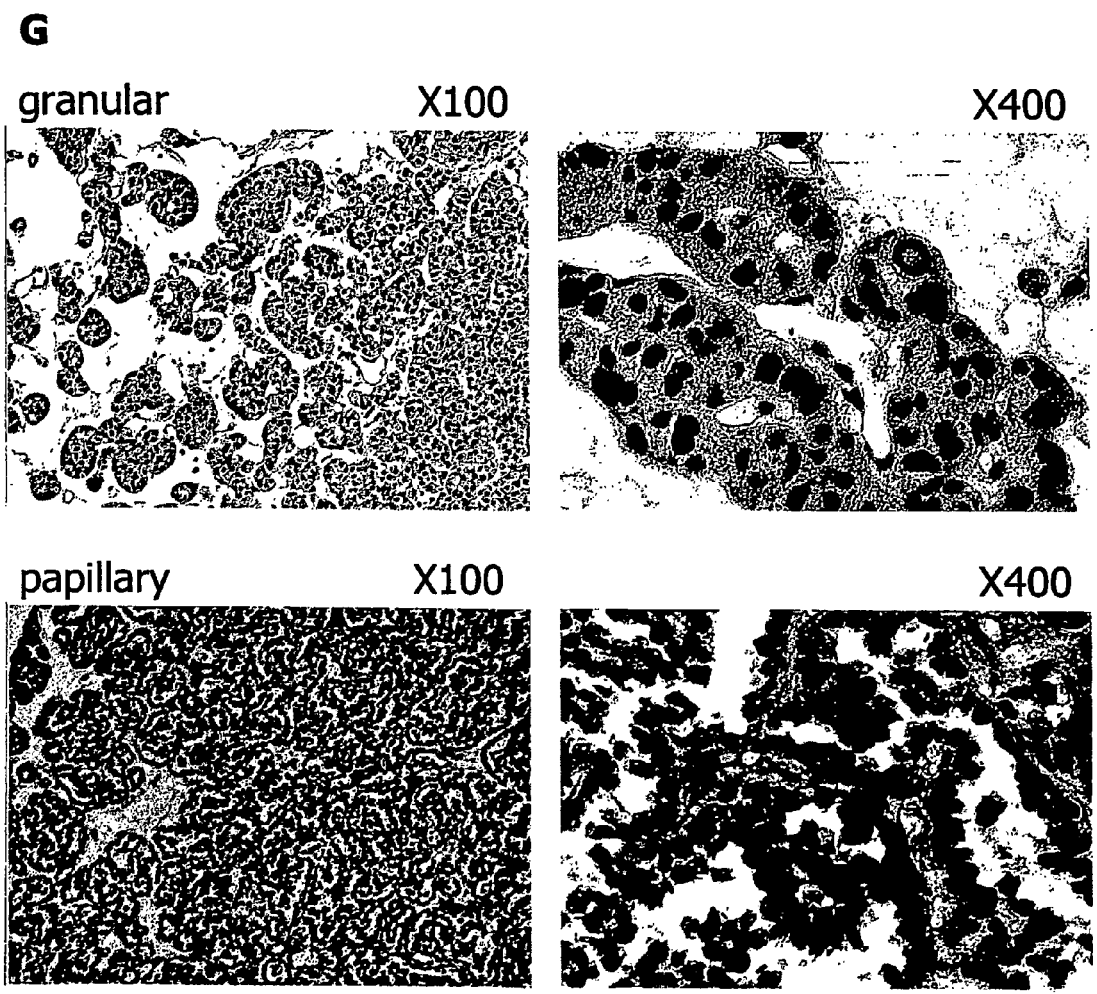
FIG. 5A are photographs depicting the suppression of endogenous HIG2 mRNA and protein expression by siRNA in an RCC cell line, caki-1.
FIG. 5B are photographs depicting the suppression of endogenous HIG2 mRNA and protein expression by siRNA in an RCC cell line, caki-2.
FIG. 5C are photographs depicting the suppression of endogenous HIG2 mRNA and protein expression by siRNA in an embryonic kidney line, HEK293.
FIG. 5D is a bar chart depicting the results of an MTT assay showing that siRNA decreased RCC and fetal kidney cell lines cell proliferation.

To determine whether HIG2 is a factor for RCC cell growth, MTT assay and colony formation assay were performed. A plasmid expression vector designed to express HIG2 was transfected into COS7 cells in which endogenous HIG2 expression was low (Mock; FIG. 4a), and established populations of cells that stably over-expressed HIG2 (stable A, B; FIG. 4a-4b). COS7-HIG2-stable showed significant enhancement of cell growth compared with the COS7 cells transfected with the control vector plasmid (FIG. 4c). This result was confirmed by three independent experiments.

Example 5

Production of HIG2 siRNA Expression Vectors

Transcription of the H1 RNA gene by RNA polymerase III produces short transcripts with uridines at the 3' ends. A genomic fragment containing the promoter region of H1 RNA was amplified by PCR using the following set of primers, 5'-TGGTAGCCAAGTGCAGGTTATA-3' (SEQ ID NO; 71), and 5'-CCAAAGGGTTTCTGCAGTTTCA-3' (SEQ ID NO; 72) and human placental DNA as a template. The product was purified and cloned into pCR2.1 plasmid vector using a TA cloning kit, according to the supplier's protocol (invitrogen). The BamHI, XhoI fragment containing H1RNA was purified and cloned into pcDNA3.1(+) between nucleotides 56 and 1257, and the fragment was amplified by PCR using primers, 5'-TGCGGATCCAGAGCAGATTGTACT-GAGAGT-3' (SEQ ID NO; 73) and 5'-CTCTATCTCGAGT-GAGGCGGAAAGAACCA-3' (SEQ ID NO; 74). The ligated DNA became the template for PCR amplification with primers, 5'-TTTAAGCTTGAAGACCATTTTTG-GAAAAAAAAAAAAAAAAAAAAAAAC-3' (SEQ ID NO; 75), and 5'-TTTAAGCTTGAAGACATGGGAAAGAGTG-GTCTCA-3' (SEQ ID NO; 76). The product was digested with HindIII and subsequently self-ligated to produce a psiH1BX vector plasmid. An siRNA expression vector against HIG2 (psiH1BX-HIG2) was prepared by cloning double-stranded oligonucleotides following as Table 4 into the BbsI site in the psiH1BX vector.

TABLE 4

| | SEQUENCE | SEQ ID NO |
|---|---|---|
| si#1 sense | 5'-TCCCGCATGTGATAAGACCTCCTTTCAAGAGAAGGAGG TCTTATCACATGC-3' | 83 |

TABLE 4-continued

| | SEQUENCE | SEQ ID NO |
|---|---|---|
| si#1 anti-sense | 5'-AAAAGCATGTGATAAGACCTCCTTCTCTTGAAAGGAGG TCTTATCACATGC-3' | 84 |
| si#2 sense | 5'-TCCCCACTGACCTAGACATGTCCTTCAAGAGAGGACAT GTCTAGGTCAGTG-3' | 85 |
| si#2 anti-sense | 5'-AAAACACTGACCTAGACATGTCCTCTCTfGAAGGACAT GTCTAGGTCAGTG-3' | 86 |
| si#3 sense | 5'-TCCCGAACCTGTCTAACTGGATGTTCAAGAGACATCCA GTTAGACAGGTTC-3' | 87 |
| si#3 anti-sense | 5'-AAAAGAACCTGTCTAACTGGATGTCTCTTGAACATCCA GTTAGACAGGTTC-3' | 88 |
| si#4 sense | 5'-TCCCCCTGTCTAACTGGATGCTCTTCAAGAGAGAGCAT CCAGTTAGACAGG-3' | 89 |
| si#4 anti-sense | 5'-AAAACCTGTCTAACTGGATGCTCTCTCTTGAAGAGCAT CCAGTTAGACAGG-3' | 90 |

The target sequences for HIG2 are:

siRNA #1
(SEQ ID NO;77)
5'-GCATGTGATAAGACCTCCT-3', siRNA #2
(SEQ ID NO;78)
5'-CACTGACCTAGACATGTCC-3', siRNA #3
(SEQ ID NO;79)
5'-GAACCTGTCTAACTGGATG-3',
and siRNA #4
(SEQ ID NO;80)
5'-CCTGTCTAACTGGATGCTC-3'.

For the control, psiH1BX3-EGFP was prepared by cloning double-stranded oligonucleotides of
(SEQ ID NO;81)
5'-TCCCGAAGCAGCACGACTTCTTCTTCAAGAGAGAAGAAGTCGTGCTG CTTC-3'
and
(SEQ ID NO;82)
5'-AAAAGAAGCAGCACGACTTCTTCTCTCTTGAAGAAGAAGTCGTGCTG CTTC-3' into the cloning site of psiH1BX3.

Example 6

HIG2 siRNA and HIG2 Antibody Inhibits Cell Growth

To determine the effect of HIG2 siRNA on cell growth, each of the above siRNA expression vectors were transfected using Lipofectamine™2000 (Invitrogen) into RCC cell lines, caki-1 and caki-2, and a human embryonic kidney cells, HEK293, which express HIG2 endogenously. After the selection by GENETICIN (Invitrogen), mode of cell proliferation was evaluated by Giemsa stain (selected for 2-weeks) and MTT assay (selected for a week) as described above, knockdown effect of HIG2 mRNA was identified by semi-quantitative RT-PCR and Western blot analyses.

The expression of the endogenous HIG2 expression was significantly suppressed by introduction of siRNA and resulted in reduction of cell growth of two RCC cells (caki-1 and caki-2) as well as human embryonic kidney cells (HEK293) (FIG. 5a-d).

Since HIG2 is secreted into culture medium by transfected COS7 cells, the protein was examined to determine whether it functions in an autocrine manner to enhance cell proliferation.

Figures 3, 4, 5, 6:
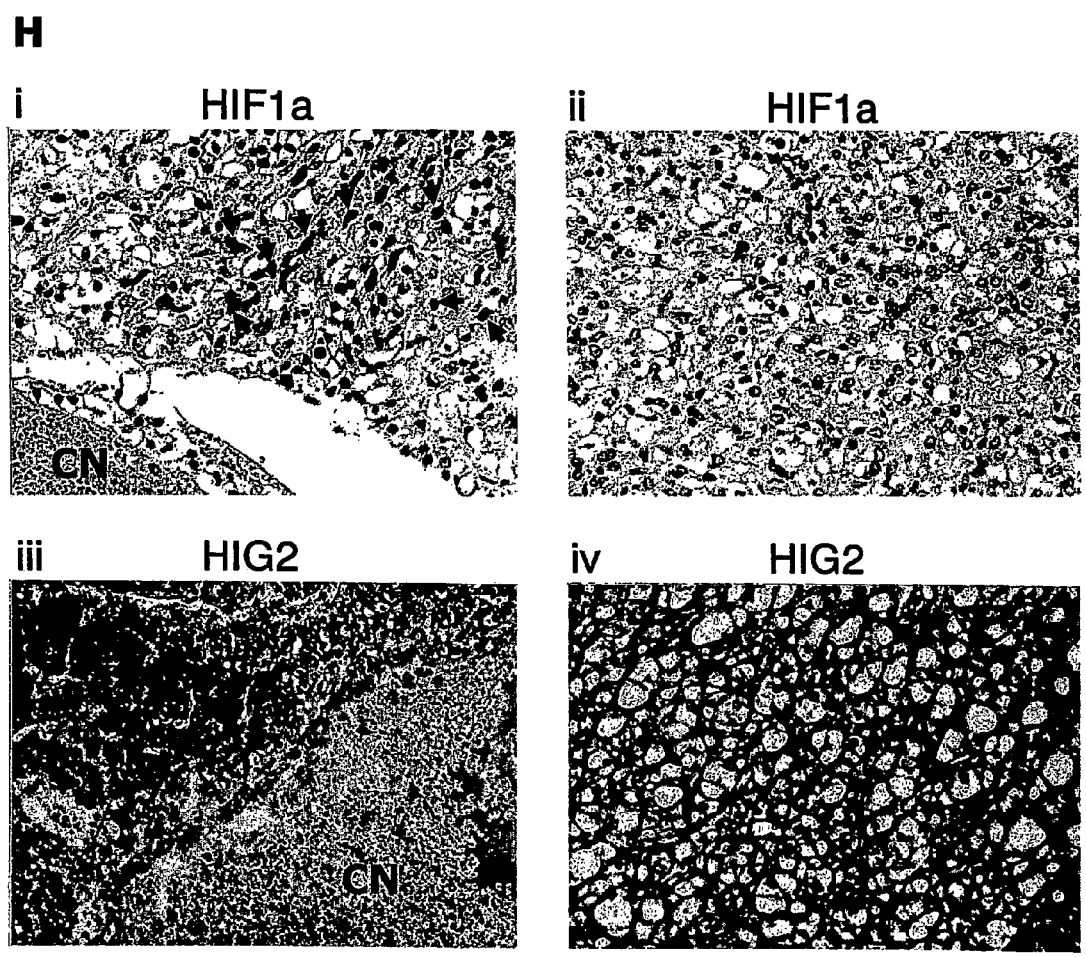
FIG. 6A is a bar chart illustrating the autocrine effect of conditioned media from COS7 cells over-expressing HIG2 promoted cell proliferation of native COS7 cells. Bars represent the average value from three experiments±SD; *, significant difference from mock ($p<0.01$) calculated by student's t-test.
FIG. 6B is a bar chart showing that recombinant hHIG2 promotes cell proliferation of native COS7 cells. Concentrations of added BSA and hHIG2 were adjusted to 1 mM. Bars represent the average value from three experiments±SD; *, significant difference from mock ($p<0.01$) calculated by student's t-test.
FIG. 6C are photographs showing inhibition of cancer cell growth by anti-HIG2 antibody. Cells were exposed for 5 days to non-immune rabbit IgG and anti-HIG2 antibody at a concentration of 1 mM, respectively.
FIG. 6D is a bar chart showing inhibition of cancer cell growth by anti-HIG2 antibody. Cells were exposed for 5 days to non-immune rabbit IgG and anti-HIG2 antibody at a concentration of 1 mM, respectively. Bars represent the average value from three experiments±SD; *, significant difference from mock ($p<0.01$) calculated by student's t-test.
FIG. 6E depicts the results of FACS analyses, which revealed that anti-HIG2 pAb facilitated RCC-specific cell death. Proportion of apoptotic cells are indicated as a percentage of sub-G1 population in FACS analysis.
Figure 4:
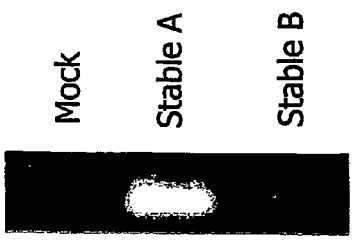
Figure 4:
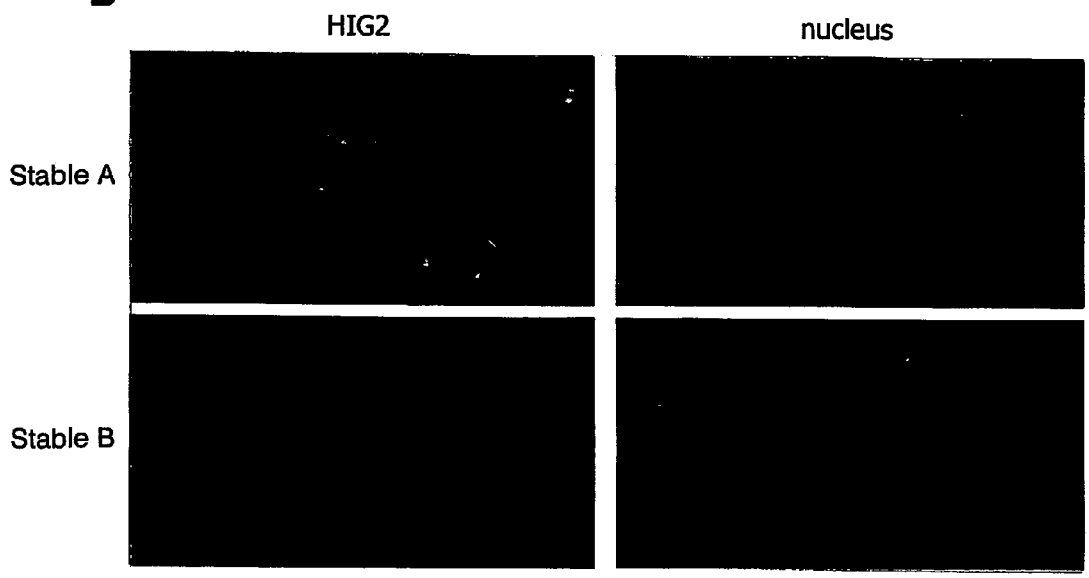
Figure 4:
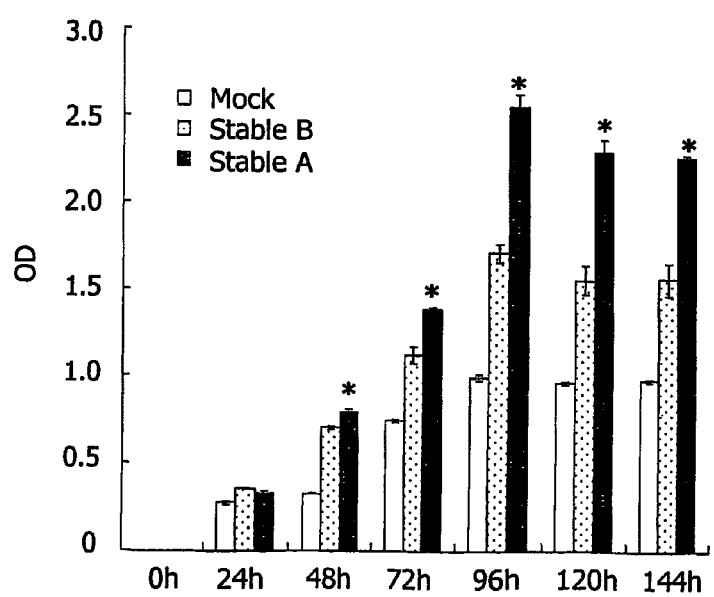
Figure 5:
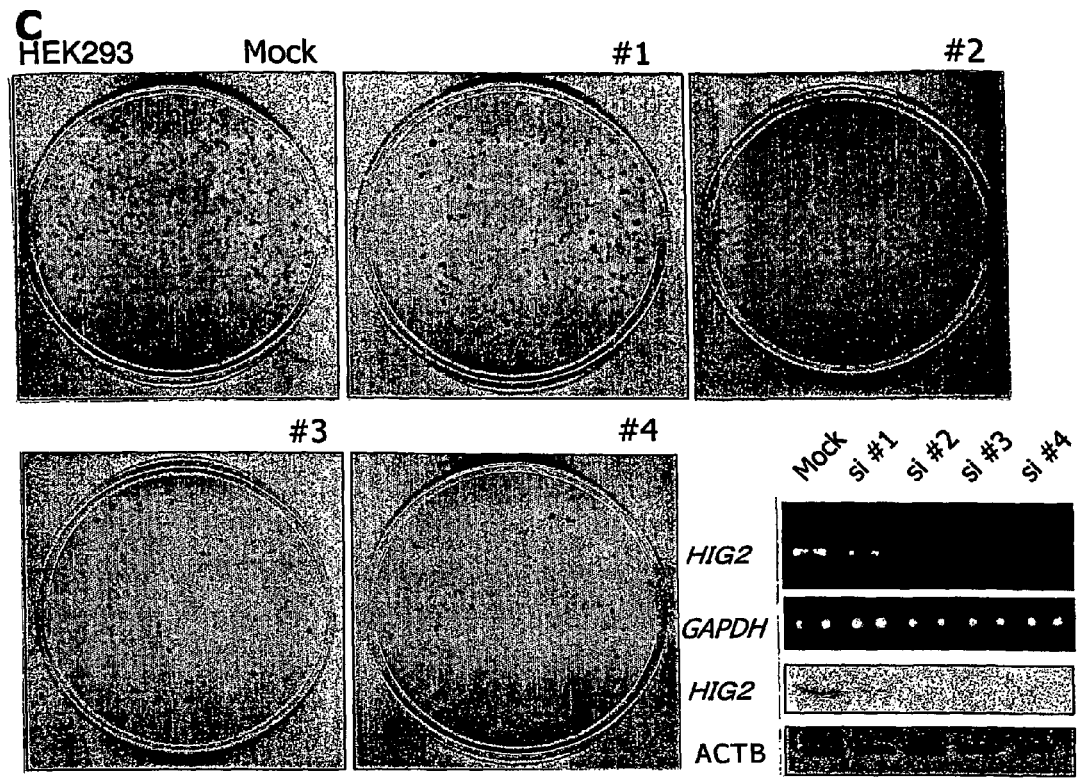
Figure 2:
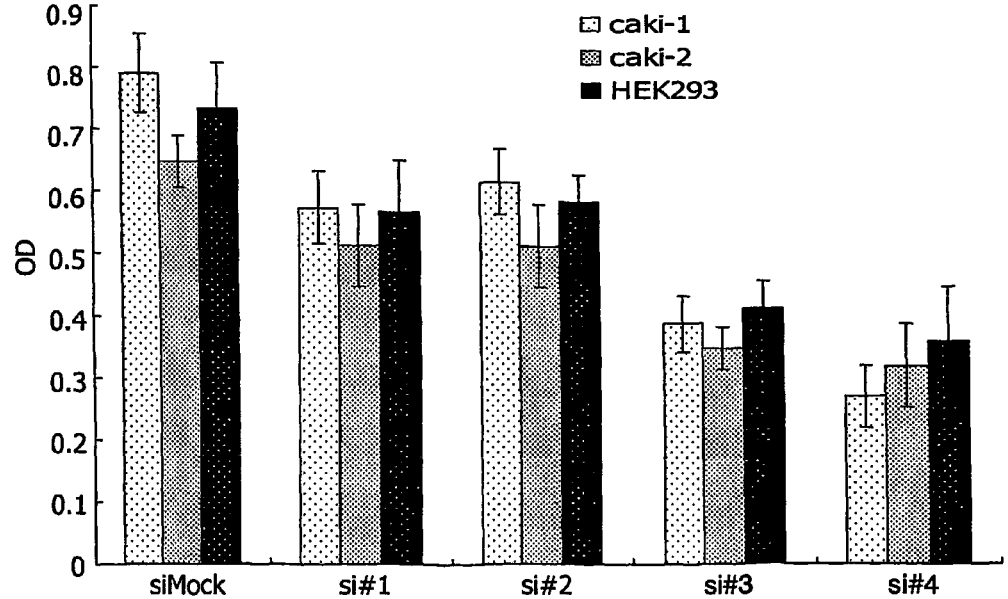
Figure 6:
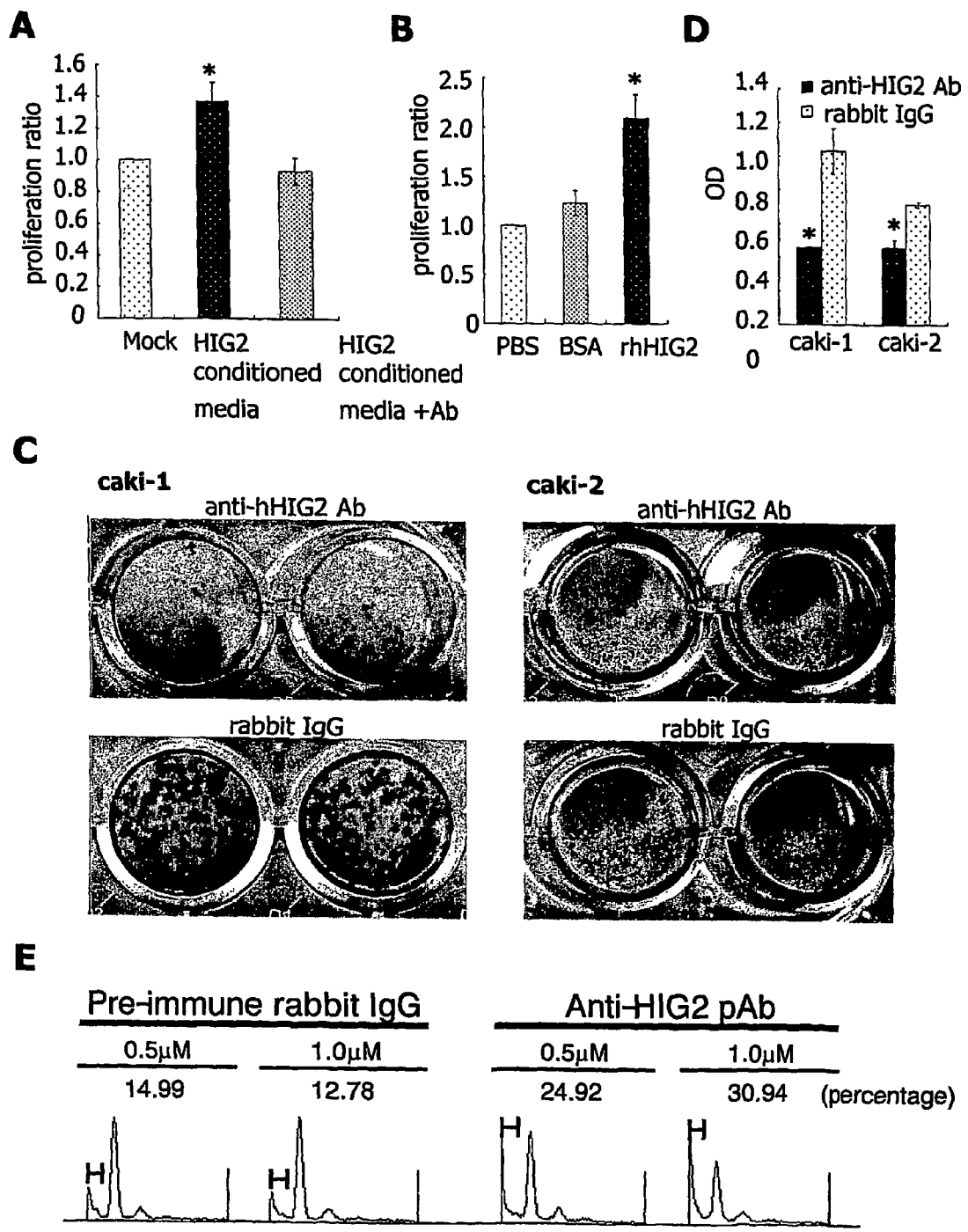

A culture media used for HIG2-overexpressing stable COS7 cells (see FIGS. 4b,c) was prepared and parental COS7 cells were cultured in the media containing using HIG2. rhHIG2 was added to the culture medium of parental COS7 cells. Both experiments revealed enhancement of cell growth (FIGS. 6a, b) and this growth-enhancing effect was neutralized by addition of anti-HIG2 pAb (FIG. 6a). Furthermore, when this antibody was added to the culture medium supporting two RCC cell lines, caki-1 and caki-2, their growth was significantly suppressed (FIGS. 6c, d).

FACS analysis was then performed using caki-1 cells treated with anti-HIG2 pAb, and it was found that anti-HIG2 pAb increased apoptotic (sub-G1) cell population of caki-1 cells in a dose dependent manner (FIG. 6e), although cancer cell lines derived from other organs were not influenced by treatment of anti-HIG2 pAb (data not shown). These results strongly support the conclusion that HIG2, a secretory molecule, functions as an autocrine growth factor that is essential for proliferation of renal tumor cells.

These results indicate that HIG2 contributes to aberrant cell growth in human cancer cells by functioning as an autocrine regulator for cell proliferation.

HIG2 is a Potential Diagnostic Marker for RCC Patients

Figure 7:
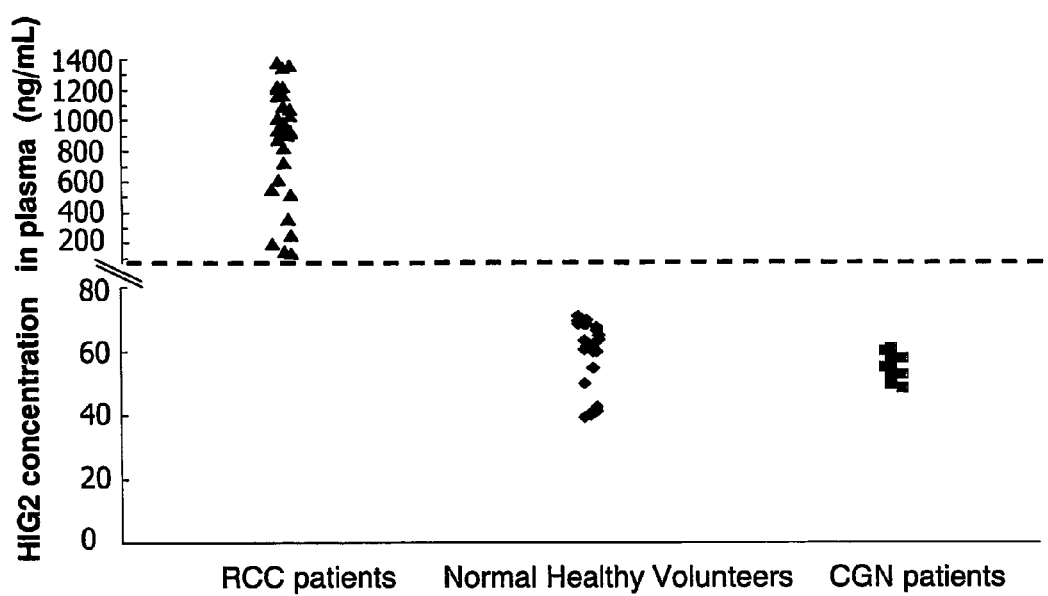
FIG. 7 depict the detection of HIG2 protein in the plasma of RCC patients. (a) HIG2 protein was observed in plasma of RCC patients exclusively by ELISA. No HIG2 protein was detected in CGN patients or normal healthy volunteers. (b) Surgical resection decreased HIG2 level in plasma of RCC patients, but not in those with metastatic tumor. Effect of tumor resection on HIG2 level in plasma was evaluated at 7 days after operation. Bars show the average value from three experiments±SD; *, significant differences from HIG2 concentration in plasma of patients before surgery ($p<0.01$).
Figure 7:
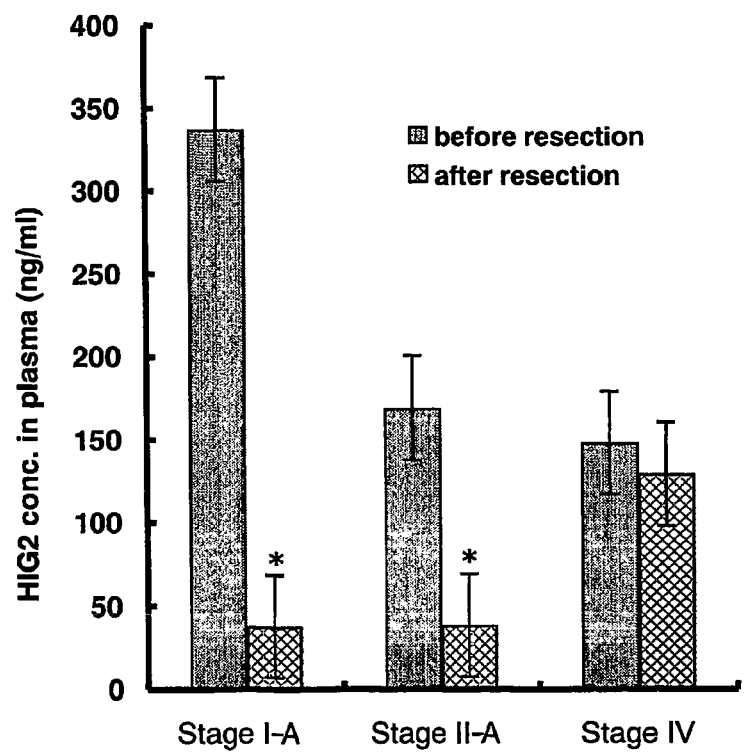

To evaluate the usefulness of HIG2 as an RCC-specific diagnostic tumor-marker, sandwich-type ELISA analysis was performed using plasma samples of 32 RCC patients as well as 20 healthy normal volunteers and 10 patients with chronic glomerulonephritis (CGN) as negative controls. Much higher levels of HIG2 protein were observed in plasma from all of the 32 RCC patients than those from all 20 healthy normal volunteers and 10 CGN patients (FIG. 7a). As expected, the HIG2 protein level in plasma of RCC patients with localized tumor dramatically decreased after surgical operation of tumors (FIG. 7b). However, the HIG2 protein level in plasma of the patients with metastatic tumor was almost unchanged even after the primary lesion was resected by surgical operation These results imply that HIG2 expression is specific to RCC and has high potential as a sensitive diagnostic marker of RCC, a cancer for which no specific tumor marker is available at present.

These results indicate that HIG2 contributes to aberrant cell growth in human cancer cells by functioning as an autocrine regulator for cell proliferation.

INDUSTRIAL APPLICABILITY

The gene-expression analysis of RCC described herein, obtained through a combination of laser-capture dissection and genome-wide cDNA microarray, has identified specific genes as targets for cancer prevention and therapy. Based on the expression of a subset of these differentially expressed genes, the present invention provides molecular diagnostic markers for identifying or detecting RCC.

The methods described herein are also useful in the identification of additional molecular targets for prevention, diagnosis and treatment of RCC. The data reported herein add to a comprehensive understanding of RCC, facilitate development of novel diagnostic strategies, and provide clues for identification of molecular targets for therapeutic drugs and preventative agents. Such information contributes to a more profound understanding of renal tumorigenesis, and provide indicators for developing novel strategies for diagnosis, treatment, and ultimately prevention of RCC.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of diagnosing clear cell renal cell carcinoma (RCC) or an increased risk for developing clear cell RCC in a human subject, comprising determining in a renal tissue sample derived from the human subject an expression level of HIG2 mRNA, wherein an increase in said level as compared to a normal human renal tissue control level of said HIG2 mRNA indicates the presence of clear cell RCC or increased risk thereof.

2. The method of claim 1, wherein said sample expression level determined is at least 10% greater than said normal human renal tissue control level.

3. The method of claim 1, wherein said method further comprises determining the expression level of a plurality of RCC-associated genes.

4. The method of claim 1, wherein said sample determining comprises detecting the hybridization of a gene probe to a gene transcript of said subject-derived renal tissue sample.

5. The method of claim 4, wherein a hybridization step is carried out on a DNA array.

6. The method of claim 1, wherein said renal tissue sample comprises a clear cell.

7. The method of claim 6, wherein said renal tissue sample comprises a clear cell from an RCC.

* * * * *